US010568992B2

(12) United States Patent
Lipke et al.

(10) Patent No.: US 10,568,992 B2
(45) Date of Patent: Feb. 25, 2020

(54) PEPTIDES FOR SUPPORTING ENDOTHELIAL PROGENITOR CELL ROLLING AND CAPTURE AND ENDOTHELIALIZATION OF BIOMATERIALS

(71) Applicant: Auburn University, Auburn, AL (US)

(72) Inventors: Elizabeth A. Lipke, Auburn, AL (US); Wen Jun Seeto, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 15/099,582

(22) Filed: Apr. 14, 2016

(65) Prior Publication Data

US 2016/0361471 A1 Dec. 15, 2016

Related U.S. Application Data

(60) Provisional application No. 62/147,215, filed on Apr. 14, 2015.

(51) Int. Cl.
| | |
|---|---|
| *A61L 31/16* | (2006.01) |
| *C12N 5/071* | (2010.01) |
| *A61L 31/04* | (2006.01) |
| *A61K 38/08* | (2006.01) |
| *A61L 27/22* | (2006.01) |
| *A61L 27/36* | (2006.01) |
| *A61L 31/00* | (2006.01) |

(52) U.S. Cl.
CPC ............ *A61L 31/16* (2013.01); *A61L 27/227* (2013.01); *A61L 27/3683* (2013.01); *A61L 31/005* (2013.01); *A61L 31/047* (2013.01); *C12N 5/069* (2013.01); *C12N 2533/30* (2013.01); *C12N 2533/50* (2013.01)

(58) Field of Classification Search
CPC ............ C12N 2533/30; C12N 2533/50; C12N 5/069; A61L 31/16; A61L 27/227; A61L 27/3683; A61L 31/005; A61L 31/047
See application file for complete search history.

(56) References Cited

U.S. PATENT DOCUMENTS

| 5,922,676 A * | 7/1999 | Pasqualini ............ A61K 38/39 424/499 |
| 5,981,478 A * | 11/1999 | Ruoslahti ............ A61L 27/227 424/484 |
| 8,426,367 B2 | 4/2013 | Patterson et al. |
| 8,691,276 B2 | 4/2014 | Badylak et al. |

OTHER PUBLICATIONS

Markway et al, Capture of Flowing Endothelial Cells Using Surface-Immobilized Anti-Kinase Insert Domain Receptor Antibody, Tissue Engineering: Part C, 2008, 14, pp. 97-105.*
Kaully et al, Vascularization: The Conduit to Viable Engineered Tissues, Advances in Tissue Engineering: Angiogenesis, 2010, pp. 17-27.*
Campbell et al, Integrin Structure, Activation, and Interactions, Cold Spring Harb Perspect Biol, 2011, 3:a004994, pp. 1-14.*
Johansson et al, Fibronectin-Integrin Interactions, Frontiers in Bioscience, 1997, 2, pp. 126-146.*
Adipurnama et al, Surface modification and endothelialization of polyurethane for vascular tissue engineering applications: a review, Biomater. Sci., 2017, 5, pp. 22-37.*
Plow et al, Ligand Binding to Integrins, The Journal of Biological Chemistry, 2000, 275, pp. 21785-21788.*
Hahn et al, Laser Scanning Lithography for Surface Micropatterning on Hydrogels, Adv. Mater., 2005, 17, pp. 2939-2942.*
Massia et al, Vascular Endothelial Cell Adhesion and Spreading Promoted by the Peptide REDV of the IIICS Region of Plasma Fibronectin Is Mediated by Integrin alpha4beta1, The Journal of Biological Chemistry, 1992, 267, pp. 14019-14026.*
RGDS Peptide, from https://www.caymanchem.com/product/15359, p. 1, accessed Dec. 13, 2017.*
Larsen et al, A biomimetic peptide fluorosurfactant polymer for endothelialization of ePTFE with limited platelet adhesion, Biomaterials, 2007, 28, pp. 3537-3548.*
Chen et al, RGD-Containing Peptides Trigger Apoptosis in Glomerular Mesangial Cells of Adult Human Kidneys, Biochemical and Biophysical Research Communications, 1997, 234, pp. 594-599.*
Koivunen et al, Isolation of a Highly Specific Ligand for the alpha5/beta1 Integrin from a Phage Display Library, The Journal of Cell Biology, 1994, 124, pp. 373-380.*
Aubin et al., "Customized interface biofunctionalization of decellularized extracellular matrix: towards enhanced endothelialization", PubMed, 2 pages Mar. 28, 2016, Abstract only.
Balaoing et al., "Laminin Peptide-Immobilized Hydrogels Modulate Valve Endothelial Cell Hemostatic Regulation", PLOS One, 16 pages Jun. 19, 2015.
Browning et al., "Multilayer vascular grafts based on collagen-mimetic proteins", Acta Biomaterialia, 12 pages Nov. 20, 2011.

(Continued)

*Primary Examiner* — Karlheinz R. Skowronek
*Assistant Examiner* — Li N Komatsu
(74) *Attorney, Agent, or Firm* — Meunier Carlin & Curfman LLC

(57) ABSTRACT

The present invention relates to the production of endothelialized matrices and materials from immature endothelial cells using substrates to which particular peptides have been grafted. The resultant substrates can be used to capture and support immature endothelial cells. Further, the methods and compositions of the present invention provide viable cell delivery platforms that allow for production and provision of endothelialized medical devices and implants, including vascular grafts, stents, shunts, and valves, endothelialized surfaces and channels for in vitro testing devices, including microfluidic chips, and materials that support vascularization such as for use in engineered tissues. The present invention includes novel methods required for the successful production of cellularized substrates, systems and components used for the same, and methods of using the resultant cell and tissue compositions.

20 Claims, 20 Drawing Sheets

Specification includes a Sequence Listing.

(56) References Cited

OTHER PUBLICATIONS

Cellular Dynamics International, "iCell Endothelial Cells User's Guide", 20 pages Aug. 1, 2015.

Choi et al., "Enhanced Patency and Endothalialization of Small-Caliber Vascular Grafts Fabricated by Coimmobilization of Heparin and Cell-Adhesive Peptides", ACS Applied Materials & Interfaces, 11 pages Jan. 29, 2016.

Jun et al., "Endothelialization of microporous YIGSR/PEG-modified polyurethaneurea", PubMed, 1 page, lasted accessed online Mar. 30, 2016, Abstract only.

Kushwaha et al., "A nitric oxide releasing, self assembled peptide amphiphile matrix that mimics native endothelium for coating implatable cardiovascular devices", Biomaterials, 7 pages Nov. 12, 2009.

Lonza, "Endothelial Cells (Normal and Diseased) & Media", 2 pages, last accessed on the internet Mar. 25, 2016.

Magin et al., "Bio-inspired 3D microenvironments: a new dimension in tissue engineering", Biomed, 13 pages Mar. 3, 2016.

de Mel et al., "Biofunctionalization of Biomaterials for Accelerated in Situ Endothelialization: A Review", American Chemical Society, vol. 9, No. 11, 11 pages Aug. 7, 2008.

Ren et al., "Surface modification and endothelialization of biomaterials as potential scaffolds for vascular tissue engineering applications", Royal Society of Chemistry, 63 pages Dec. 14, 2014.

Songstad et al., "Generating iPSC-Derived Choroidal Endothelial Cells to Study Age-Related Macular Degeneration", Investigative Ophthalmology & Visual Science, 10 pages Nov. 3, 2015.

Veleva et al., "Combinatorial Selection of Cell-Specific Peptides by Phage Display Experiments", NSTI-Nanotech 2005, vol. 2005, 4 pages, last accessed online Mar. 30, 2016.

Veleva et al., "Selective endothelial cell attachment to peptide-modified terpolymers", Biomaterials 29 (2008), 6 pages Jun. 16, 2008.

Wang et al., "Adhesion of Endothelial Cells and Endothelial Progenitor Cells on Peptide-Linked Polymers in Shear Flow", Department of Chemical and Biomolecular Engineering, 9 pages Jun. 28, 2013.

Zhou et al., "Promoting endothelialization on decellularized porcine aortic valve by immobilizing branched polyethylene glycolmodified with cyclic-RGD peptide: an in vitro study", Biomedical Materials, 13 pages Nov. 20, 2015.

\* cited by examiner

| | Shear Rate (1/s) | | | |
|---|---|---|---|---|
| Peptide | 20 | 40 | 80 | 120 |
| CRRETAWAC (SEQ ID NO: 1) | 131.6±16.3 | 278.4±28.6 | 550.6±64.1 | 828.4±82.7 |
| P11 | 127.5±18.4 | 251.0±41.2 | 508.0±86.5 | 787.6±102.1 |
| PRb | 110.3±17.7 | 235.0±36.1 | 485.7±67.5 | 735.1±102.6 |
| REDV (SEQ ID NO: 2) | 78.6±15.8 | 183.3±43.4 | 353.8±82.0 | 564.3±177.0 |
| RGDS (SEQ ID NO: 3) | 102.2±20.1 | 218.7±42.4 | 455.8±86.7 | 739.7±121.9 |
| YIGSRG (SEQ ID NO: 4) | 103.2±18.9 | 223.2±38.0 | 487.6±72.5 | 737.0±107.9 |

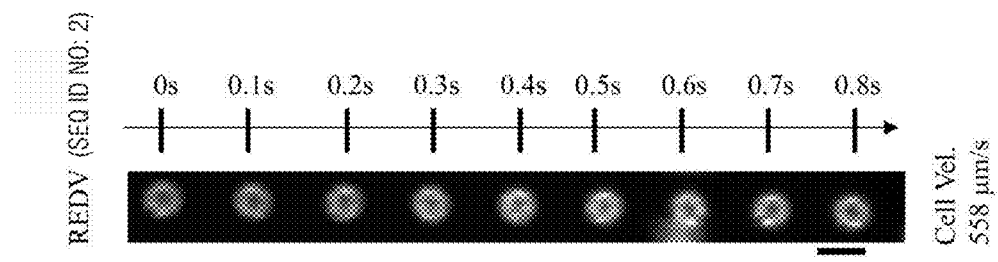
*FIG. 16A*
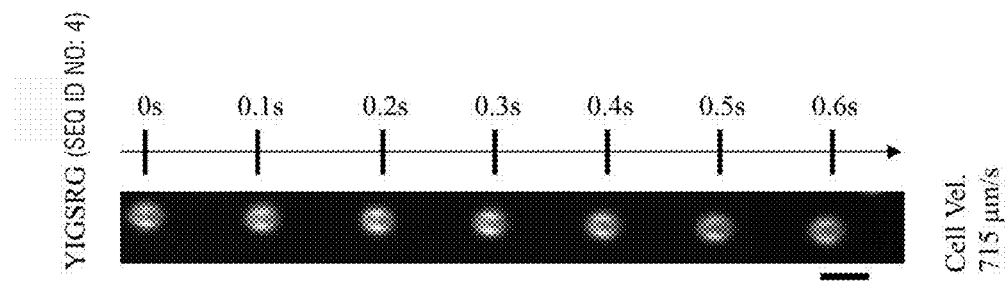
*FIG. 16B*
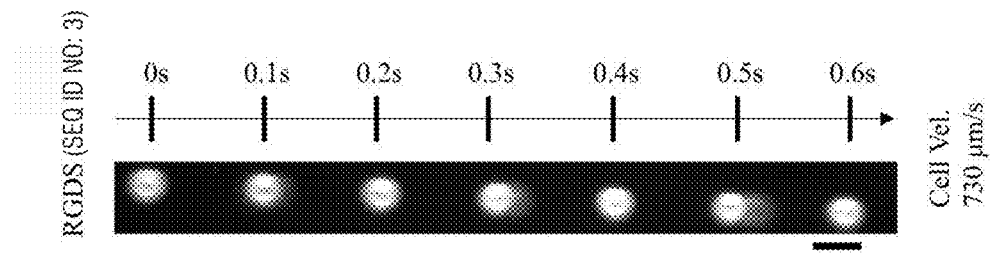
*FIG. 16C*
*FIG. 16*

SEQUENCE LISTING

<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Synthesized peptide -continued

```
<400> SEQUENCE: 1

Cys Arg Arg Glu Thr Ala Trp Ala Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Synthesized peptide

<400> SEQUENCE: 2

Arg Glu Asp Val
1

<210> SEQ ID NO 3
<211> LENGTH: 4
<212> TYPE: PRT
<213> ORGANISM: Artificial Sequence
<220> FEATURE:
<223> OTHER INFORMATION: Synthesized peptide

<400> SEQUENCE: 3

Arg Gly Asp Ser
1

<210> SEQ ID NO 4
<211> LENGTH: 6
<212> TYPE: PRT
<213> ORGANISM: Artificial Sequence
<220> FEATURE:
<223> OTHER INFORMATION: Synthesized peptide

<400> SEQUENCE: 4

Tyr Ile Gly Ser Arg Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Synthesized peptide

<400> SEQUENCE: 5

Arg Gly Glu Ser
1

<210> SEQ ID NO 6
<211> LENGTH: 27
<212> TYPE: DNA
<213> ORGANISM: Artificial Sequence
<220> FEATURE:
<223> OTHER INFORMATION: N represents any nucleotide (A, C, G, or T) and
      K represents either G or T
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
```

<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 6
tgtnnknnkn nknnknnknn knnktgt                                    27

<210> SEQ ID NO 7
<211> LENGTH: 13
<212> TYPE: PRT
<213> ORGANISM: Artificial Sequence
<220> FEATURE:
<223> OTHER INFORMATION: Synthesized peptide

<400> SEQUENCE: 7

Gly Ser Ser Ser Cys Arg Arg Glu Thr Ala Trp Ala Cys
1               5                   10

<210> SEQ ID NO 8
<211> LENGTH: 24
<212> TYPE: PRT
<213> ORGANISM: Artificial Sequence
<220> FEATURE:
<223> OTHER INFORMATION: Synthesized peptide; Xaa is 16 carbons-glutamic
      acid-2 carbons
<220> FEATURE:
<221> NAME/KEY: PEPTIDE
<222> LOCATION: (1)..(1)
<223> OTHER INFORMATION: Xaa is 16 carbons-glutamic acid-2 carbons

<400> SEQUENCE: 8

Xaa Lys Ser Ser Pro His Ser Arg Asn Ser Gly Ser Gly Ser
1               5                   10                  15

Gly Ser Gly Arg Gly Asp Ser Pro
            20

<210> SEQ ID NO 9
<211> LENGTH: 5
<212> TYPE: PRT
<213> ORGANISM: Artificial Sequence
<220> FEATURE:
<223> OTHER INFORMATION: Synthesized peptide

<400> SEQUENCE: 9

Pro His Ser Arg Asn
1               5

<210> SEQ ID NO 10
<211> LENGTH: 10
<212> TYPE: PRT
<213> ORGANISM: Artificial Sequence
<220> FEATURE:
<223> OTHER INFORMATION: Synthesized peptide

<400> SEQUENCE: 10

Ser Gly Ser Gly Ser Gly Ser Gly Ser Gly
1               5                   10

```
<210> SEQ ID NO 11
<211> LENGTH: 6
<212> TYPE: PRT
<213> ORGANISM: Artificial Sequence
<220> FEATURE:
<223> OTHER INFORMATION: Synthesized peptide

<400> SEQUENCE: 11

His Ser Asp Val His Lys
1               5

<210> SEQ ID NO 12
<211> LENGTH: 20
<212> TYPE: PRT
<213> ORGANISM: Artificial Sequence
<220> FEATURE:
<223> OTHER INFORMATION: Synthesized peptide

<400> SEQUENCE: 12

Asn Cys Lys His Gln Cys Thr Cys Ile Asp Gly Ala Val Gly Cys Ile
1               5                   10                  15

Pro Leu Cys Pro
            20

<210> SEQ ID NO 13
<211> LENGTH: 6
<212> TYPE: PRT
<213> ORGANISM: Artificial Sequence
<220> FEATURE:
<223> OTHER INFORMATION: Synthesized peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 13

His Xaa Xaa Xaa His Lys
1               5

<210> SEQ ID NO 14
<211> LENGTH: 11
<212> TYPE: PRT
<213> ORGANISM: Artificial Sequence
<220> FEATURE:
<223> OTHER INFORMATION: Synthesized peptide

<400> SEQUENCE: 14

Arg Gly Asp Ser His His His His His His Gly
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthesized peptide

<400> SEQUENCE: 15

Val Ile Leu Val Leu Phe Gly
1               5

<210> SEQ ID NO 16
<211> LENGTH: 4
<212> TYPE: PRT
<213> ORGANISM: Artificial Sequence
<220> FEATURE:
```

```
<223> OTHER INFORMATION: Synthesized peptide

<400> SEQUENCE: 16

Gly Ser Ser Ser
1

<210> SEQ ID NO 17
<211> LENGTH: 10
<212> TYPE: PRT
<213> ORGANISM: Artificial Sequence
<220> FEATURE:
<223> OTHER INFORMATION: Synthesized peptide

<400> SEQUENCE: 17

Cys Arg Arg Glu Thr Ala Trp Ala Cys Gly
1               5                   10

<210> SEQ ID NO 18
<211> LENGTH: 20
<212> TYPE: PRT
<213> ORGANISM: Artificial Sequence
<220> FEATURE:
<223> OTHER INFORMATION: Synthesized peptide

<400> SEQUENCE: 18

Pro His Ser Arg Asn Ser Gly Ser Gly Ser Gly Ser Gly Ser Gly Arg
1               5                   10                  15

Gly Asp Ser Gly
            20

<210> SEQ ID NO 19
<211> LENGTH: 7
<212> TYPE: PRT
<213> ORGANISM: Artificial Sequence
<220> FEATURE:
<223> OTHER INFORMATION: Synthesized peptide

<400> SEQUENCE: 19

His Ser Asp Val His Lys Gly
1               5

<210> SEQ ID NO 20
<211> LENGTH: 21
<212> TYPE: PRT
<213> ORGANISM: Artificial Sequence
<220> FEATURE:
<223> OTHER INFORMATION: Synthesized peptide

<400> SEQUENCE: 20

Asn Cys Lys His Gln Cys Thr Cys Ile Asp Gly Ala Val Gly Cys Ile
1               5                   10                  15

Pro Leu Cys Pro Gly
            20

<210> SEQ ID NO 21
<211> LENGTH: 6
<212> TYPE: PRT
<213> ORGANISM: Artificial Sequence
<220> FEATURE:
<223> OTHER INFORMATION: Synthesized peptide

<400> SEQUENCE: 21

Val Ile Leu Val Leu Phe
1               5
```

PEPTIDES FOR SUPPORTING ENDOTHELIAL PROGENITOR CELL ROLLING AND CAPTURE AND ENDOTHELIALIZATION OF BIOMATERIALS

CROSS-REFERENCE TO RELATED APPLICATIONS

This application claims priority under 35 U.S.C. § 119 to provisional application Ser. No. 62/147,215 filed Apr. 14, 2015, herein incorporated by reference in its entirety.

GRANT REFERENCE

This invention was made with government support under NSF-CBET-1150854 awarded by National Science Foundation, and 14SDG18610002 awarded by the American Heart Association. The government has certain rights in the invention.

SEQUENCE LISTING

The instant application contains a Sequence Listing which has been submitted electronically via EFS-Web in ASCII format and is hereby incorporated by reference in its entirety. Said ASCII copy, created on Jun. 29, 2016, is named LIPKE_15099582_P11793US01_SEQUENCES_ST25.txt and is 4,826 bytes in size.

FIELD OF THE INVENTION

The present invention is directed to compositions and methods for the capture and support of immature endothelial cells. More particularly, the invention is directed to endothelialization of a substrate, including medical devices and implants. The capture and support of immature endothelial cells relies on the presence of two or more peptides or proteins, as described herein, grafted to the surface of the substrate.

BACKGROUND OF THE INVENTION

Endothelial progenitor cells (EPCs) and pluripotent stem cell-derived endothelial cells have the potential to become a reliable source of autologous cells for endothelialization of intravascular devices and vascularization of tissue engineered constructs. In order to design biomaterials that can employ EPCs to enhance endothelialization, however, a better understanding of their dynamic adhesion to material surfaces under physiological shear is needed.

Endothelial colony forming cells (ECFCs) are one type of EPCs; ECFCs are highly proliferative and are capable of forming mature and functional endothelial cells for vessel repair and postnatal angiogenesis. EPCs are a subpopulation of monocytes that are derived from myeloid cells, which are one type of leukocyte. EPCs that have been isolated from blood and expanded in vitro are frequently called late outgrowth or endothelial colony forming cells (ECFCs). Expression of surface receptors on these cells differs from other types of monocytes, "early outgrowth" EPCs, and mature endothelial cells. Advantages of ECFCs for tissue engineering applications include the relative ease and lack of comorbidity in obtaining autologous cells, the highly proliferative nature of ECFCs, and the ability of ECFCs to yield mature endothelial cells. To exploit their potential, however, it is necessary to first understand whether ECFCs behave similarly to ECs in their abilities to interact with engineered biomimetic materials and which cell surface receptors mediate these interactions.

As a precursor for endothelial cells (ECs), EPCs show an endothelial-like phenotype with high proliferative capability (especially late EPCs), and can be differentiated into mature endothelial cells that form the endothelium. Hence, potential clinical applications of EPCs include vessel repair, neovascularization of ischemic organs, and coating of vascular grafts. Previous work has shown that β2 integrins are important in EPC homing to sites of ischemia and neovascularization. Integrins also play an important role in EPC capture on EC or ECM proteins in vitro. Although the types and distribution of integrin receptors are not well identified on EPCs, prior work has estimated the number of $\alpha_5\beta_1$ and $\alpha_v\beta_3$ integrin receptors present on umbilical cord-blood derived EPC using flow cytometry. Besides flow cytometry, investigation of EPC migration has shown that blocking as $\alpha_5\beta_1$ decreases EPC migration. However, understanding of the constitution and function of integrins present on the membrane surface of EPCs is still very limited and needs to be further explored. Importantly, although it was known that ECFCs express as $\alpha_5\beta_1$ and $\alpha_v\beta_3$ integrins, ECFCs were not known to express an integrin that would bind REDV (SEQ ID NO:2) (discussed below).

Cardiovascular disease is one of many conditions that may be treated by the insertion of stents and/or vascular grafts. However, incomplete endothelialization can reduce the effectiveness of this type of treatment. Therefore, the incorporation of endothelium specific factors, for example, tailoring biomaterials for cardiovascular implant coatings, will provide enhanced clinical treatment alternatives. One such coating includes a nanofibrous matrix that may be applied to the medical implant as a self-assembled coating. Other such materials include biomimetic materials and polymer coatings for implants and medical devices.

Previous work has attempted to identify and characterize peptides, including REDV (SEQ ID NO:2), RGDS (SEQ ID NO:3), and YIGSRG (SEQ ID NO:4), grafted on PEG hydrogels have been shown to support EPC rolling under shear. Despite the fact that REDV (SEQ ID NO:2)-grafted hydrogels reduced EPC rolling velocity the most, however, it does not support firm adhesion even at low shear rate. Thus, there is a continuing need for peptides that are capable of slowing and capturing EPCs. Notably, REDV (SEQ ID NO:2) (which binds $\alpha_4\beta_1$), does not bind either $\alpha_5\beta_1$ and $\alpha_v\beta_3$ integrin, which are expressed on EPCs and pluripotent stem cell-derived endothelial cells.

CRRETAWAC (SEQ ID NO:1)

The peptide CRRETAWAC (SEQ ID NO:1) has a high binding affinity and selectivity for integrin $\alpha_5\beta_1$. Prior work involved constructing a heptapeptide library by ligating a synthetic oligonucleotide into fUSE 5 vector. The oligonucleotide has a core sequence of TGT(NNK)7TGT (SEQ ID NO:6) where N represents an equal molar mixture of A, C, G, T while K represents G or T. TGT was coded for cysteine and NNK was coded for all amino acid. The cysteines on each side of the peptide were designed to form disulfide bond and to form cyclic peptides. Thus, the oligonucleotide produces a library of cyclic peptides with seven random amino acids. When the peptide library was screened with α5β1 coated wells to identify the peptide with high binding affinity with α5β1, among the non-RGD containing peptides, CRRETAWAC (SEQ ID NO:1) showed the highest affinity to α5β1.

Other previous works has investigated CRRETAWAC (SEQ ID NO:1) in endothelialization of expanded polytetrafluoroethylene (ePTFE) surfaces by incorporating GSSS-CRRETAWAC (SEQ ID NO:7) (FIG. 4). When ePTFE was modified with GSSSCRRETAWAC (SEQ ID NO:7), it supported EC attachment and proliferation under static conditions. Furthermore, a significant lower coverage of the surface by platelets was observed comparing to RGD surface and FN-coated glass. More notably, use of this peptide for capture of cells from physiological flow conditions has not previously been considered.

—(C16)2-Glu-C2-KSSPHSRNSGSGSGSGSGRGDSP (SEQ ID NO:8) (PR_b) for α5β1

Despite the fact that PRb contained the ubiquitous RGD peptide and the synergistic PHSRN (SEQ ID NO:9) peptide, this peptide is chosen to test for the capability on EPC rolling due to the its superior design in accurately mimicking FN's binding affinity for $\alpha_5\beta_1$. This peptide has been shown to mimic FN through HUVEC adhesion, spreading, and extracellular FN production (Mardilovich et al., 2006). In native FN, the distance between PHSRN (SEQ ID NO:9) and RGD is 30-40 Å which is a critical factor for PHSRN (SEQ ID NO:9) to perform its synergistic role in adhesion. With the length for each amino acid being 3.7 Å, the Kokkoli Lab used SGSGSGSGSG (SEQ ID NO:10), which is a total of 10 amino acids to give a linker distance of 37 Å, to match the distance between PHSRN (SEQ ID NO:9) and RGD. In addition, it has been shown that the ratio of hydrophilic to hydrophobic residues in between PHSRN (SEQ ID NO:9) and RGD in FN is almost 1:1 (Mardilovich & Kokkoli, 2004). The repeating SG sequence was chosen to mimic this ratio. Therefore, PRb was able to mimic the adhesion property of FN for α5β1.

HSDVHK (SEQ ID NO:11) (P11)

P11 was discovered by screening through PS-SPCL using protein-protein competitive inhibition assay. The PS-SPCL that was studied was comprised of 114 types of hexapeptide mixture and this library was divided into 6 groups with each group has various amino acids residues at each position. The PS-SPCL together with fluorescently labeled vitronectin (VN) were added onto $\alpha_v\beta_3$-coated surface and allowed to compete for the $\alpha_v\beta_3$ integrin. As shown in FIG. 5, peptides with histidine, H, at Position 1 showed the lowest fluorescent intensity meaning it was highly competitive for $\alpha_v\beta_3$ and inhibited the fluorescently labeled VN to bind $\alpha_v\beta_3$. Similarly, histidine at Position 5 and lysine, K, at position 6 showed the same result. On the other hand, more than one amino acid showed similar result at Position 2, 3, and 4. Therefore, 12 hexapeptides with sequence HXXXHK (SEQ ID NO:13) were synthesized where X represents glycine/histidine/serine at Position 2, aspartic acid/leucine at Position 3, and leucine/valine at Position 4. These 12 hexapeptides were further screened using the same competitive inhibition assay and HSDVHK (SEQ ID NO:11) was found to be the most competitive for $\alpha_v\beta_3$. Thus, HSDVHK (SEQ ID NO:11) has a high specificity and affinity for $\alpha_v\beta_3$ and it has high potential in capturing $\alpha_v\beta_3$-expressing EPCs.

NCKHQCTCIDGAVGCIPLCP (SEQ ID NO:12) (V2)

V2 is a peptide representing the 116-135 residues of the cysteine-rich heparinbinding protein (CCN1). The functions of CCN1 include regulating cell adhesion, migration, proliferation, survival and differentiation in mesenchymal cells. Studies have shown that CCN1 binds directly to $\alpha_v\beta_3$ and mediates pro-angiogenic activities. Previous studies have evaluated peptides of different portion of CCN1 and reported that V2 was responsible portion for HUVEC adhesion specifically through $\alpha_v\beta_3$. Previous work has also shown that when the D residue was altered into A, the altered V2 peptide lost the capability to bind HUVEC through $\alpha_v\beta_3$ integrin. Furthermore, shorter versions of V2 have also shown similar results meaning V2 is the exact peptide required to bind $\alpha_v\beta_3$. Therefore, V2 is a potential peptide to capture EPCs due to its specific binding to $\alpha_v\beta_3$.

BRIEF SUMMARY OF THE INVENTION

The present invention relates to previously unknown peptides and combinations of peptides that significantly increase the capture rate of endothelial cells, including endothelial colony forming cells (ECFCs) under flow conditions with physiological shear rates. The endothelial cell capturing peptides may include CRRETAWAC (SEQ ID NO:1) and PRb (SEQ ID NO: 8). The combination may further involve an endothelial cell slowing peptide REDV (SEQ ID NO:2) and an endothelial cell capturing peptide CRRETAWAC (SEQ ID NO:1). REDV (SEQ ID NO:2) has shown to significantly decrease ECFC rolling velocity compared to other bioactive peptides, including RGDS (SEQ ID NO:3), YlGSRG (SEQ ID NO:4), P11 (SEQ ID NO: 11), PRb (SEQ ID NO: 8), and CRRETAWAC (SEQ ID NO:1). Despite the fact that REDV (SEQ ID NO:2)-grafted hydrogels had the greatest reduction in EPC rolling velocity, REDV (SEQ ID NO:2) does not support capture even at low shear rates. Surprisingly, however, cell capture events were consistently observed on CRRETAWAC (SEQ ID NO:1)-grafted hydrogels and on PRb (SEQ ID NO: 8), grafted hydrogels at 20 s$^{-1}$. In our analysis, 3.74%±1.0% of ECFCs were captured on CRRETAWAC (SEQ ID NO:1)-grafted hydrogels and 1.14%±0.2% of ECFCs were captured on PRb grafted hydrogels. To further evaluate the potential use of CRRETAWAC (SEQ ID NO:1) in the ECFC capture for endothelialization, ECFC rolling on hydrogels that were grafted with combinations of CRRETAWAC (SEQ ID NO:1) with REDV (SEQ ID NO:2), which has a high affinity for the integren $\alpha_4\beta_1$, were assessed. Hydrogels grafted with REDV (SEQ ID NO:2)/CRRETAWAC (SEQ ID NO:1) combination (0.35 μmol/μL of REDV (SEQ ID NO:2)/0.35 pmol/ml of CRRETAWAC (SEQ ID NO:1)) had significantly increased ECFC capture of 13.4%±2.3% as compared to CRRETAWAC (SEQ ID NO:1) alone. Thus, we have discovered the peptides CRRETAWAC (SEQ ID NO:1) and PRb and the combination of CRRETAWC(SEQ ID NO:1)/REDV (SEQ ID NO:2) for capturing ECFCs under shear including potential use in establishing or recovering the vascular endothelium.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3(A-F) shows inhibition of integrin $\alpha_5\beta_1$-FN interaction by a hexapeptide PS-SPCL. Generally, the y-axis represents the relative fluorescence intensity of fluorescently-labeled FN that was bound to the integrin $\alpha_5\beta_1$ coated ProteoChip, while the x-axis represents the peptides with different amino acids at the corresponding position. The amino acids at each position of the hexapeptide that substantially inhibited the binding of the fluorescently labeled FN to $\alpha_5\beta_1$ are highlighted by boxes. As indicated on each sub-figure the lower the relative fluorescence intensity, the higher the binding affinity of the peptide to $\alpha_5\beta_1$.

FIG. 5(A-F) shows inhibition of integrin $\alpha_v\beta_3$-VN by a hexapeptide PS-SPCL. Generally, the y-axis represents the relative fluorescence intensity of fluorescently-labeled VN bound to the integrin $\alpha_v\beta_3$ coated ProteoChip, while the x-axis represents the peptides with different amino acids at the corresponding position. The amino acids at each position of the hexapeptide that substantially inhibited the binding of the fluorescently labeled VN to $\alpha_v\beta_3$ are highlighted by boxes.

FIG. 7(A-B) shows ECFC rolling velocity between novel peptides and known ECM peptides. As each shear rate, conditions that do not share the same letter are significantly different (p<0.05) from each other based on Tukey's test. Data represent mean±SD (n=3).

FIG. 16(A-C) shows a series of extracted frames following a representative ECFC through the flow chamber on (A) REDV (SEQ ID NO:2)-, (B) RGDS (SEQ ID NO:3)-, and (C) YIGSRG (SEQ ID NO:4)-grafted hydrogels. Scale bar=30 µm.

Figure 1:
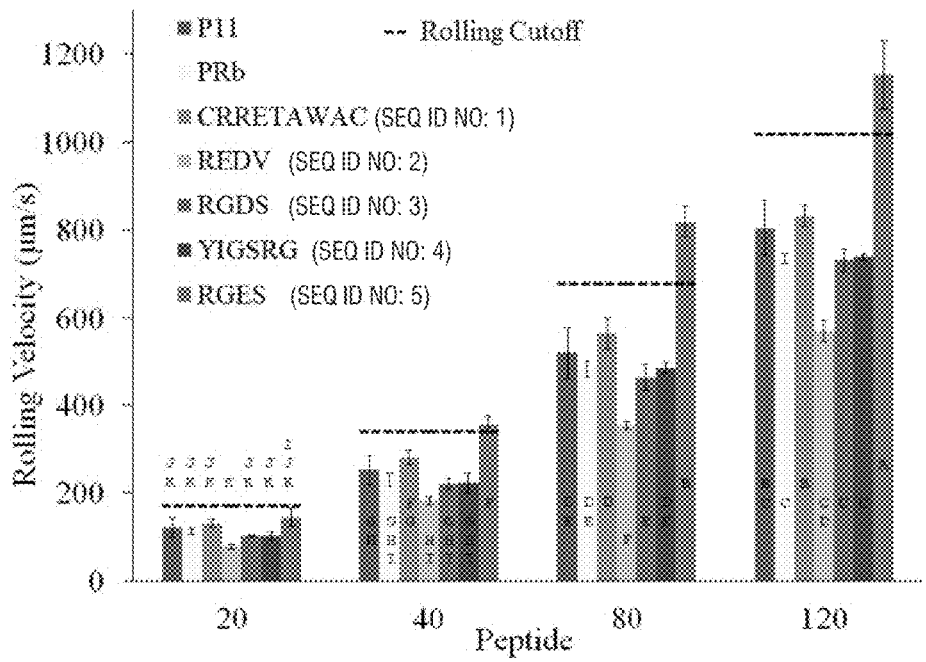
FIG. 1 shows ECFC rolling velocities on peptide-grafted PEG hydrogels. REDV (SEQ ID NO:2)-grafted hydrogels had significantly lower ECFC rolling velocities. Means that do not share the same letter are significantly different (p<0.05).

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The following definitions and introductory matters are provided to facilitate an understanding of the present invention.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

"Biomimetic materials" refers to materials which act to emulate properties from a natural biological environment. Such materials may be selected based on one or more characteristics, including, for example, ability to maintain the mechanical and electrical properties of the native tissue, direct cell and tissue orientation, deliver particular drugs and growth factors, and degrade in response to enzymes secreted by cells. Furthermore, these materials can be selected based on ability to promote cell adhesion, mechanical stretch and electrical conduction. Overall, biomimetic materials can be engineered or selected to produce functional tissue with highly controlled, defined properties. Examples of biomimetic materials include natural materials and synthetic materials. Natural materials include, but are not limited to, materials derived from proteins, polysaccharides, and other derivatives of these substances, such as, for example, collagen, gelatin, glycosaminoglycans (e.g. hyaluronic acid), elastin, fibronectin, laminin, fibrin, and alginates. Synthetic materials include temporally-changing or externally-modifiable materials that can be engineered to provide biomimetic properties that facilitate cardiac regeneration. Materials that fall into this category are unique in their ability to change structure based on changes in input (temperature, pH, photoactive, mechanical/electrical stress hydrogels, environmentally-responsive polymers, and conductive materials.

The term "crosslink" refers to a bond or chain of atoms attached between and linking two different polymer chains.

"Endothelialized" and "endotheliazation" refer to formation of a coating layer of endothelial cells. Endotheliazation may include protecting underlying materials or large vessels that have sustained damage, such as from blood flow, and may also include prevention of restenosis by inhibiting overgrowth of other cell types, particularly in the case of stents and other implants.

"Enriching," as the term is used herein, refers to the process by which the concentration, number, or activity of something is increased from a prior state. For example, a population of 100 ECFCs is considered to be "enriched" in ECFCs if the population previously contained only 50 ECFCs. Similarly, a population of 100 ECFCs is also considered to be "enriched" in ECFCs if the population previously contained 99 ECFCs. Likewise, a population of 100 ECFCs is also considered to be "enriched" in ECFCs even if the population previously contained zero ECFCs.

The terms "graft" and "grafting" generally refer to the attachment or conjugation of two or more materials. With respect to the present invention, grafting refers to any process or method by which a protein or peptide can be attached to a polymer, substrate, matrix or material.

The term "hydrogel" refers to a water-swellable polymeric matrix, consisting of a three-dimensional network of macromolecules held together by covalent crosslinks that can absorb a substantial amount of water to form an elastic gel.

As the term is used herein, "isolated" refers to a polynucleotide, polypeptide, protein, molecule, compound, material or cell of genomic or synthetic origin or some combination thereof which is not associated with all or a portion of the polynucleotides, polypeptides, proteins, molecules, compounds, materials or cells with which the isolated polynucleotide, polypeptide, protein, molecule, compound, material or cell is found in nature, or is linked to a polynucleotide, polypeptide, protein, molecule, compound, material or cell to which it is not linked in nature.

"Maintenance" of a cell or a population of cells refers to the condition in which a living cell or living cell population is neither increasing nor decreasing in total number of cells in a culture. Alternatively, "proliferation" of a cell or population of cells, as the term is used herein, refers to the condition in which the number of living cells increases as a function of time with respect to the original number of cells in the culture.

The term "operably linked" as used herein refers to the joining, coupling, or linking of a peptide to a surface through a wide range of chemistries into an equally large number of different materials. A peptide can be operably linked to a surface, for example, by grafting, bonding, coating, linking, crosslinking, polymerizing, co-polymerizing, or integrating. For example, one or more peptides may be incorporated into a substrate material as the substrate material is being formed, such as incorporation into a nanofibrous matrix or a multi-layer vascular graft.

The term "PEG" as used herein refers to poly(ethylene glycol).

The phrase "pluripotent stem cells" (PSCs) refers to stem cells that have the potential to differentiate into any of the three germ layers: endoderm (interior stomach lining, gastrointestinal tract, the lungs), mesoderm (muscle, bone, blood, urogenital), or ectoderm (epidermal tissues and nervous system). PSCs of the present invention include embryonic PSCs and induced PSCs, which are derived from a non-pluripotent cell, typically an adult somatic cell, generated by any method known in the art, including, for example, through introduction or activation of specific transcription factors and/or genes.

As the term is used herein, "population" refers to two or more cells.

The term "physiological shear" refers to the frictional force tangential to the direction of a flowing fluid, the force of which is directly related to the fluid's viscosity shear stress. In blood vessels, shear stress acts on endothelium and is the mechanical force responsible for the acute changes in luminal diameter.

A "somatic cell" is understood to be a biological cell ordinarily found in a multicellular organism that is not a gamete, germ cell, gametocyte, or undifferentiated stem cell. Somatic cells include cells of the endoderm (interior stomach lining, gastrointestinal tract, the lungs), mesoderm (muscle, bone, blood, urogenital), and ectoderm (epidermal tissues and nervous system).

"Substantially homogeneous," as the term is used herein, refers to a population of a substance that is comprised primarily of that substance, and one in which impurities have been minimized.

"Vascularization" is the process of new blood vessel formation, including vessel formation to support wound healing, perfusion of engineered tissues.

Cellularization Compositions

In one aspect, the present invention involves compositions for inducing rolling and stopping of immature endothelial cells. In a further aspect, the compositions are effective for cellularization, specifically endothelialization and vascularization. In one aspect, the compositions comprise a substrate to which is grafted two or more peptides or proteins that mediate rolling, capture, and support of immature endothelial cells under physiological shear.

Peptides and proteins suitable for the compositions and methods of the present invention are generally adhesion ligand peptides and peptides capable of binding integrins. In a further aspect, the proteins and peptides are capable of binding to $\alpha_5\beta_1$, $\alpha_4\beta_1$, or $\alpha_v\beta_3$ cell surface integrin. In one embodiment, the proteins or peptides comprise one or more proteins or peptides capable of binding to $\alpha_5\beta_1$ or $\alpha_v\beta_3$ cell surface integrin, and one or more proteins or peptides capable of binding $\alpha_4\beta_1$. In another embodiment, the proteins or peptides are selected from the group consisting of CRRETAWAC (SEQ ID NO:1), YIGSRG (SEQ ID NO:4), REDV (SEQ ID NO:2), RGDS (SEQ ID NO:3), P11 (SEQ ID NO: 11), and PRb (SEQ ID NO: 8). In an even more preferred embodiment, the compositions and methods of the present invention involve two or more peptides, most preferably comprising CRRETAWAC (SEQ ID NO:1) and REDV (SEQ ID NO:2) or PRb (SEQ ID NO: 8), and REDV (SEQ ID NO:2). In a further aspect, proteins and peptides of the invention include proteins and peptides that incorporate any of CRRETAWAC (SEQ ID NO:1), YIGSRG (SEQ ID NO:4), REDV (SEQ ID NO:2), RGDS (SEQ ID NO:3), P11 (SEQ ID NO: 11), and PRb (SEQ ID NO: 8).

According to one aspect of the invention, the compositions and methods include a substrate (i.e. a surface, matrix or material) operably linked to one or more of the peptides described herein. In one further aspect, the substrate can be a polymer compatible with cellular vascularization. In another aspect, the substrate is a biomimetic matrix or material, including materials suitable for use in medical devices or implants, including but not limited to vascular grafts.

In one aspect, the substrate can be a synthetic polymer-based material, such as expanded poly(tetrafluoroethylene) and poly-(ethylene terephthalate) (Dacron). In another aspect, biomimetic materials for use in the present invention include biomaterials that can be engineered or selected to produce functional tissue with highly controlled, defined properties. Examples of biomimetic materials include natural materials and synthetic materials, or a combination of natural materials and synthetic materials. Examples of biomaterials can be found in U.S. Pat. No. 8,691,276, titled "Extracellular matrix-derived gels and related methods" which is incorporated herein in its entirety. Natural materials include, but are not limited to, materials derived from proteins, polysaccharides, and other derivatives of these substances, such as, for example, collagen, gelatin, glycosaminoglycans (e.g. hyaluronic acid), elastin, fibronectin, laminin, fibrin, and alginates. Synthetic materials include temporally-changing or externally-modifiable materials that can be engineered to provide biomimetic properties that facilitate cardiac regeneration. Examples of biomimetic materials include, but are not limited to, polycaprolactone (PCL), poly(glycolic acid) (PGA), poly-4-hydroxybutyrate (P4HB), poly (lactic acid) (PLA) and poly(lactic-co-glycolic acid) (PLGA), poly(glycerol-sebacate) (PGS), poly(trimethylene carbonate-co-lactide), polyester urethane urea (PEUU)129, Pluronic F127/GelMA, HA/N-cadherin mimetic peptides, MaHA/MMP-degradable crosslinker/BMP-2, fibrin/PDGF-BB/BMP-2, PEGDMA, expanded polytetrafluoroethylene (ePTFE), poly(ethylene terephthalate) (PET) and polyurethanes (PU), biodegradable polymers such as poly(lactide-co-glycolide), poly(ethylene glycol)-b-poly(L-lactide-coe-caprolactone) and polydepsipeptides, polyurethane and combinations thereof; and copolymers of natural and synthetic materials. Materials that fall into this category are unique in their ability to change structure based on changes in input (temperature, pH, photoactive, mechanical/electrical stress hydrogels, environmentally-responsive polymers, and conductive materials). Other artificial extracellular matrix proteins that can be used for, or compose part of, substrates of the present invention include recombinant cellulose-binding domain (CBD)-RGD fusion protein, GFOGER.

In another aspect, the substrate comprises natural polymers and biomimetic materials. Natural polymers include ECM-derived collagen, fibronectin, laminin, hyaluronic acid, and vitronectin. An exemplary natural or synthetic biomimetic material includes hydrogels. Hydrogels are insoluble, cross-linked polymer network structures composed of hydrophilic homo- or hetero-co-polymers, which have the ability to absorb significant amounts of water. Consequently, this is an essential property to achieve an immunotolerant surface and matrix (i.e., with respect to protein adsorption or cell adhesion). Due to their significant water content, hydrogels also possess a degree of flexibility very similar to natural tissue, which minimizes potential irritation to surrounding membranes and tissues. In general, hydrogels are strong hydrophiles, capable of supporting nutrient transport and controlled degradation to allow for cell proliferation, generally composed of self-assembling materials, namely peptide amphiphiles. Hydrogels are highly absorbent (they can contain over 90% water) natural or synthetic polymeric networks. Hydrogels also possess a degree of flexibility very similar to natural tissue, due to their significant water content. Hydrogels for use in the present invention include both entangled hydrogels and covalently linkable hydrogels. In a further aspect, covalently-linkable hydrogels are used as the biomimetic material based on advantageous characteristic, including, for example, the ability to reproducibly form three-dimensional structures using molds or deposition techniques. Covalently-linkable hydrogels include all aqueous-based covalently-linkable hydrogels, including all hydrogels formed from natural polymers and hydrogels formed from synthetic polymers. Covalently linkable hydrogels also include PEG-based (polyethylene glycol) and non-PEG-based polymers; non-PEG-based hydrogels include both natural and synthetic hydrogels. In a most particular aspect, hydrogels of the present invention can be composed of PEGylated fibrinogen, where the naturally occurring component fibrinogen is directly coupled to acrylated PEG to form PEG-fibrinogen. In another aspect, the biomimetic material of the present invention can be an acrylated gelatin.

In certain aspects, the substrate may comprise decellularized extracellular matrix (dECM), such as decellularized ovine pulmonary heart valve cusps (dPVCs) and decellularized rat aortic grafts (dAoGs).

In one aspect, the methods of the present invention can include modulation of the mechanical properties of a hydrogel for different types of cells and/or tissues. In addition, the methods can use state-of-the-art soluble factors and/or media formulations to drive formation of a variety of somatic cells and tissues. In one aspect, the methods can be used to generate cardiac cells or tissues. In another aspect, for example, the methods can be used to generate neural tissue formation, using similar PEG-fibrinogen crosslinking density and/or mechanical properties as those used for production of cardiac cells and tissues, but different soluble factors and media formulation. The density and crosslinking properties of PEG-fibrinogencan be varied by one or more of the following: crosslinking time/light intensity, concentration of PEG-fibrinogen, inclusion of a porogen (e.g. gelatin beads), or addition of 1% or 2% PEG-diacrylate (with or without a matrix metalloproteinase degradable peptide segment, such as acryl-PEG-degradable_peptide-PEG-acryl).

The compositions of the present invention may comprise additional elements that can aid in cell capture, cell support, and/or cell maintenance. Additional components include additional cell adhesion peptides, such as RGDS (SEQ ID NO:3) and YIGSRG (SEQ ID NO:4), heparin, fibrinogen/fibrin, fibronectin, collagen/gelatin, albumin, laminin, the tripeptide Arg-Gly-Asp (RGD), stem cell factor (SCF; c-kit ligand), and CXCR2 ligand. The compositions may also include additional peptides for binding outgrowth endothelial cells, as described in U.S. Pat. No. 8,426,367.

In a further aspect of the invention, the peptides described herein are operably linked to the surface of the substrate. In one embodiment, the peptides can be operably linked to the substrate by incorporation into the substrate material. In another aspect, the peptides can be operably linked to the substrate through grafting, including by any method known in the art, such as various physical, chemical, and biofunctionalization techniques, which can also be combined. For example, the grafting can be passive adsorption or covalent grafting. Physical and chemical modification can be used to influence protein and peptide adsorption. Proteins and peptides can also be grafted to the substrate surface using biofunctionality, including passive coating, covalent linking, and presenting peptide linkers to sequence specific peptides from the environment. Chemical modifications that may be used for coupling proteins or peptides to substrates are summarized in Table 1.

TABLE 1

| Peptide or protein reactive group | Coupling or cross-linking reagent | Substrate surface functional group |
|---|---|---|
| —NH$_2$ | cyanogen bromide cyanuric chloride DMT-MM | —OH |
| —NH2—OH | glutaraldehyde succinate anhydride diisocyanate compounds diisothoncyanate compounds | —NH$_2$ |
| —NH2 —SH | nitrous acid | —NH$_2$ |
| —Ph—OH | hydrazine and nitrous acid | |
| —COOH | DMT-MM carbodiimide compounds (EDC, DCC) | —NH$_2$ |
| —SH | disulfide compound | —SH |
| —NH2 | thionyl chloride N-hydroxysuccinimide | —COOH |

TABLE 1-continued

| Peptide or protein reactive group | Coupling or cross-linking reagent | Substrate surface functional group |
|---|---|---|
| | N-hydroxysulfosuccinimide + EDC | |

DCC, dicyclohexylcarbodiimide;
DMT-MM, 4(4,6-dimethoxy-1,3,5-triazin-2-yl)-4-methylmorpholinium chloride;
EDC, 1-ethyl-3-(3-dimethylaminopropyl) carbodiimide hydrochloride Capture of Endothelial Cells and Support of Endothelial Cells Under Physiological Shear In another aspect, the present invention involves methods for capture of immature endothelial cells and support of endothelial cells under physiological shear. In one aspect, a source of endothelial cells is exposed to a substrate that comprises one or more integrin-binding peptides. The peptides can be operably linked to the substrate, for example by grafting to the surface of the substrate, coupling to the substrate, or incorporation into the substrate. Sources of endothelial cells include, immature endothelial cells, endothelial progenitor cells embryonic stem cell-derived endothelial cells, pluripotent stem cell-derived endothelial cells, induced pluripotent stem cell-derived endothelial cells and adult stem cell sources, such as adipose derived stem cells, mesenchymal stem cells, and bone marrow derived stem cells. In a further aspect, sources of immature endothelial cells may include a homogenous population or fraction of cells, or may include a heterologous population of more than one cell type or fraction of cells. The sources of immature endothelial cells may primary endothelial cells, such as primary coronary artery cells, primary aortic endothelial cells, primary pulmonary artery endothelial cells, primary umbilical vein endothelial cells, and primary dermal microvascular endothelial cells, or cell lines such as SK-HEP-1 cells, HUVEC cells, TeloHAEC cells, EA.hy926 cells, TIME cells, NFκB-TIME cells, HMEC-1 cells, HULEC-5a cells. Endothelial cells can be identified or characterized by gene and protein expression (including, for example, CD31, CD105, CD144, ZO-1, and von Willebrand Factor) and endothelial cell functions (including, for example, tubular network formation, acetylated LDL uptake, barrier function, and wound healing).

Sources of immature endothelial cells used in the present invention can also include cells present in or isolated from a subject. Samples that can be obtained from a subject for use in the present invention include blood or blood parts (i.e. cell pellet or cell fractions obtained by density gradient centrifugation), tissue homogenates, or ex vivo expanded cell populations derived from a sample. The samples can be enriched for immature endothelial cells, for example, by fractionation, density gradient centrifugation, flow cytometry, cell sorting, and the like.

In a further aspect, the methods involve capture of immature endothelial cells by the peptides or proteins grafted to the substrate. Capture is carried out by exposing the cells to the substrate bearing the peptides under conditions that will permit cell attachment to the substrate. In one embodiment, immature endothelial cells are seeded directly onto the substrate. The cells can be seeded at 1,000-100,000 cells/cm', depending on the source of endothelial cells. For example, a cell fraction obtained from blood may require a higher seeding density, while a population of cells obtained by primary cell culture may require a lower seeding density, due to the relative numbers of immature endothelial cells present in each source. In another aspect, the exposure may occur under fluid flow conditions. In one embodiment, the cells and substrate may be subjected to physiological shear.

In another aspect, the present methods can be used to capture immature endothelial cells in vivo. Thus, the source of immature endothelial cells may be the blood of the subject in vivo.

Populating a Substrate Surface with Peptides to Capture and Support Immature Endothelial Cells In another aspect, the present invention involves methods for producing substrates or materials that selectively bind endothelial progenitor cells. In a particular aspect, the methods comprise providing a substrate. The substrate or material can be composed of any substance that will support cell capture and maintenance, including polymers, hydrogels, and other biomimetic matrices and materials, as discussed herein. In one embodiment, the substrate is a material suitable for a medical device or implant, such as a biomimetic material. In another embodiment, the substrate is a polymer for coating for an implant or medical device.

The methods further comprise operably linking one or more peptides to the surface of the substrate. In one aspect of the methods, the proteins and peptides of the present invention are grafted to the surface of a substrate. Grafting of the proteins of peptides can be accomplished through any process or method known in the art, including, for example, incorporating the peptides into the substrate material, or crosslinking, photocrosslinking, bioconjugation, and polymerization. In an exemplary embodiment, proteins or peptides may be grafted to the surface of a PEG hydrogel by conjugation of the protein or peptide to acryloyl-PEG-SVA to produced PEG-peptides, which may then be incorporated into the surface of the PEG hydrogel through polymerization of the PEG. In another embodiment, the proteins or peptides are incorporated into the substrate material, such as by incorporation into a nanofibrous matrix or multilayer vascular graft. In another embodiment, the proteins or peptides are incorporated into a coating that is placed onto a substrate, for example an implant or medical device.

Substrates that can be used for methods of the present invention include polymers as described herein, as well as matrices and materials, and especially biomimetic materials that form medical devices or implants. In one aspect, the substrate can be a coating on a material or matrix, for example a PEG hydrogel coating on the surface of a polymer. In another aspect, the substrate can be a biomimetic material, such that no coating is required for grafting of the proteins or peptides.

In a further aspect, substrates can include surfaces and channels for in vitro testing devices, such as microfluidic chips, and materials that support vascularization such as for use in engineered tissues.

Medical Device Coatings

In yet another aspect, the compositions of the present invention may be applied to medical implants or devices. Medical implants according to the present invention are preferably vascular grafts, including stents, shunts, and valves. In one aspect, a polymer compatible with cellular vascularization is applied to or coupled to a surface of a medical implant or device that is comprised of a matrix or material. The application of a polymer to the matrix or material forming the medical implant or device can be, for example, through incorporation of the peptides into the polymer material. Preferred applications include the augmentation of existing systems and/or polymers for medical device and implant coatings, which are in long-standing commercial use. These existing systems and polymers fail frequently, due in many cases to large extent as a results of lack of endotheliazation. Additional long-term applications include use in tissue engineered products. The application of a polymer to the matrix or material forming the implant or medical device can also be, for example, through interfacial photopolymerization with the matrix or material. Matrices or materials for medical devices or implants can include those intended for tissue engineering, including biomimetic materials. Specific applications include vascular grafts, vascularization of synthetic biomaterial, and next generation stenting.

To support vasularization and vascular re-endothelialization and vascular re-endotheliazation, the compositions may comprise materials currently used for intravascular materials. Materials used in vivo to support vascularization and re-endotheliazation include biomimetic materials that are able to maintain adherent cells on their surfaces under physiological shear stress, support migration and proliferation of mature endothelial cells from the ends of the lesion, and provide appropriate ligands for the rolling and eventual firm adhesion of endothelial colony forming cells (ECFCs). In a further aspect, therefore, the medical implants of the present invention may further comprise two or more peptides and combinations of peptides as described herein. Inclusion of the peptides significantly increase the capture rate of ECFCs under shear. The combination of peptides includes an ECFC slowing peptide and an ECFC capturing peptide. The peptides may be one or more of CRRETAWAC (SEQ ID NO:1), REDV (SEQ ID NO:2), RGDS (SEQ ID NO:3), YlGSRG, P11 (SEQ ID NO: 11), and/or PRb (SEQ ID NO: 8). In a preferred embodiment, the peptides are directly incorporated into a polymer, which is in turn applied to or coupled to the matrix or material forming the medical device or implant. Alternatively, the peptides can be grafted to the matrix or material forming the medical device or implant.

In one aspect, the matrix or material used for the medical device or implant comprises a nanofibrous matrix comprising two different peptide amphipiles (PAs), which can include one or more of the peptide described herein, such as REDV (SEQ ID NO:2). PBr (SEQ ID NO: 8), and/or CRRETAWAC (SEQ ID NO:1). In an alternative embodiment, a multilayer vascular graft may include a one or more of the described peptides conjugated into a poly(ethylene glycol)(PEG) hydrogel to generate bioactive hydrogels that bind to endothelial cells (ECs). The peptide-incorporating hydrogel may be reinforced with an electrospun polyurethane mesh to achieve suitable biomechanical properties. A functional small-caliber vascular graft must have suture retention strength sufficient for immediate implantation as well as requisite long-term burst strength. In addition, graft compliance is not only important in matching the physical and bulk mechanical characteristics of native arteries; it has a large effect on preventing reocclusion of grafts. As mesh thickness is increased, the maximum force that can be sustained, or suture retention strength in this case, increases. Mesh thickness has a similar effect on burst pressure of vascular grafts.

In a preferred embodiment, electrospinning may be utilized for fabricating the segmented polyurethane mesh sleeve because this process produces fibrous, porous scaffolds with mechanical properties which can be broadly tailored via modification of electrospinning parameters. The ability to tune the biomechanical properties of electrospun segmented polyurethanes to improve matching to those of native vasculature is important in preventing intimal hyperplasia and thrombosis-induced failure in small diameter grafts.

Vascularization

In another aspect, the present invention involves vascularization of engineered tissues and biomimetic materials. The compositions of the present invention can be applied to implants and medical devices, which are then exposed to endothelial cells. The implants and or medical devices are then incubated with the endothelial cells under conditions that permit blood vessel formation. Such conditions may occur in vitro, through cell and tissue culture, or in vivo, through implantation.

In Vitro Applications

In a further aspect the invention involves in vitro applications of the described compositions and methods. In one aspect, the described peptides can be integrated onto microfluidic chips, which can be used for drug testing devices. Incorporation of the peptides onto such microfluidic chips can be performed as described elsewhere for other substrates. In addition, it is contemplated that the integration can be through processes such as protein "printing" and 3D printing. In a further aspect, the chips can the undergo endotheliazation, to produce chips operably linked to endothelial cells to allow the devices to test drug response.

Cell Capture and Diagnosis

In another aspect the compositions and methods of the invention can be used for cell capture and diagnosis techniques. In one aspect, the proteins and peptides and be used for targeted delivery to ECFCs, for example for delivery of cancer therapeutics. The proteins or peptides can be operably linked to a drug-delivery system, such as a particle, nanosphere, or liposome, allowing for specific targeting of endothelial cells, including ECFCs. In another aspect, the compositions can be applied to methods of sorting or separating endothelial cells from a mixed population of cells, for example through magnetic affinity cell sorting (MACS). The proteins or peptides can be operably linked to magnetic nanoparticles to preferentially attach to the endothelial cells expressing the molecule to which the proteins or peptides bind. In another aspect, the described compositions can be used for diagnostics, for example through identification of specific cells that bind the proteins or peptides as described. The proteins or peptides can be conjugated to a marker or indicator, such as streptavidin or a fluorophore, which allows for specific detection. Cells to which the conjugated proteins or peptides bind can then be readily detected using known techniques.

EXAMPLES

Example 1: Peptide Grafted Hydrogels to Capture Endothelial Progenitor Cells Under Shear for Endothelialization In this study, late outgrowth endothelial colony forming cells (ECFCs), a type of EPCs, were investigated based on their advantages for use in endothelialization; ECFCs can be isolated from adult blood, they proliferate rapidly, and they can become mature ECs. Poly(ethylene glycol) diacrylate (PEG-DA) was chosen as the base material to test ECFC dynamic adhesion; PEG-DA is able to resist protein adsorption and therefore served as a "blank slate" for testing adhesion ligands. Peptides, including RGDS (SEQ ID NO:3), REDV (SEQ ID NO:2), YIGSRG (SEQ ID NO:4), CRRETAWAC (SEQ ID NO:1), P11 (SEQ ID NO: 11), PR_b (SEQ ID NO: 8), and RGES (SEQ ID NO:5), were grafted on the surface of the PEG-DA hydrogels. Interactions between ECFCs and the peptides were assessed in two ways: dynamic adhesion and maintenance of adhesion under shear. Through observation and quantification of ECFC rolling and retention on peptide grafted hydrogels under shear, dynamic and static adhesion between ECFCs and peptides was evaluated.

Methods:

Umbilical cord blood ECFCs were used in this study. To create the peptide-grafted PEG surfaces, PEG-DA was first photopolymerized to form a hydrogel base. Peptides were conjugated to acryloyl-PEG-SVA to produced the PEG-peptides, and 0.7 µmol/mL of each PEG-peptide was grafted onto the surface of the PEG hydrogel base. Shear experiments were performed to examine ECFC rolling and adhesion on the hydrogel surfaces. Using a Glycotech parallel plate flow chamber, the ECFC cell suspension was sheared over the hydrogels at shear rates of $20\ s^{-1}$, $40\ s^{-1}$, $80\ s^{-1}$, and $120\ s^{-1}$. Cell rolling events were recorded at 70 fps using a high speed camera. Cell tracking was performed using ImageJ and Matlab to determine rolling velocities. Finally ECFC retention on the RGDSQ ID NO:3)-grafted PEG hydrogels was quantified under superphysiological shear stress.

PEG Peptide Conjugation

Peptides, either synthesized or purchased (American Peptide), were first conjugated to acryloyl-PEG-succinimidyl valerate (acryloyl-PEG-SVA, 3400 Da; Laysan Bio) and then grafted onto PEGDA hydrogels. Peptides, including RGDS (SEQ ID NO:3), RGES (SEQ ID NO:5), RGDSH-HHHHG (SEQ ID NO:14), YIGSRG (SEQ ID NO:4), and REDV (SEQ ID NO:2), were first dissolved in sodium bicarbonate buffer (0.04 mg/µL, pH 8.5). Acryloyl-PEG-SVA was then dissolved in 1 mL of 50 mm sodium bicarbonate buffer (pH 8.5) for every 10 mg of peptide to be reacted. The final peptide:acryloyl-PEG-SVA molar ratio was 1.2:1. The peptide solution was immediately added dropwise to the acryloyl-PEG-SVA solution with mild vortexing. The mixture was allowed to react for 4 hrs at room temperature in the dark with constant mixing. The resulting acryloyl-PEG-peptide was then dialyzed (molecular weight cutoff 500-1,000, Spectrum Labs) and lyophilized for storage under argon at −80° C. in a brown glass vial.

PEG Peptide Conjugation and Confirmation Through Mass Spectrometry

Peptide synthesis was confirmed by mass spectrometry. A small amount of peptide (<1 mg) was dissolved in 10% acetonitrile and 0.1% formic acid injection solution. Result mass was obtained using Q-TOF Premier (Waters, Milford, Mass.) and shown in Appendix A.

Hydrogel Grafting with Peptides

To form the PEG-peptide grafting solution, the acryloyl-PEG-peptide was first dissolved in sterile PBS at the desired concentration (ranging from 0.7 mM to 5.6 mM) and the photoinitiator was added as described above. After each PEGDA hydrogel was photocrosslinked, the top plate of the mold was removed. The hydrogels were rinsed with sterile PBS and briefly dried with a stream of nitrogen to remove excess PBS on the surface of the hydrogel. The mold's 0.5 mm PDMS spacers were replaced with 0.7 mm PDMS spacers and a clean glass slide was placed on top. Then the PEG-peptide grafting solution was injected between the hydrogel and the new piece of glass and photocrosslinked to the top of the PEGDA hydrogel under the UV lamp for 7 min. PEG-peptide grafted hydrogels were then rinsed and swollen in sterile PBS for experiments.

Figure 2:
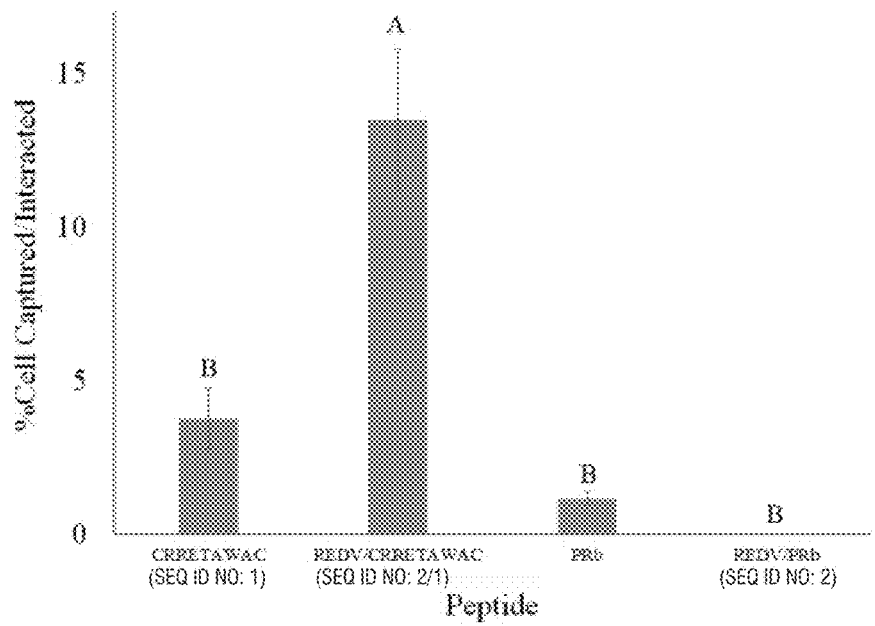
FIG. 2 shows ECFC captured rate on CRRETAWAC (SEQ ID NO:1), PRb (SEQ ID NO: 8), and with REDV (SEQ ID NO:2) combinations.
Figure 3A:
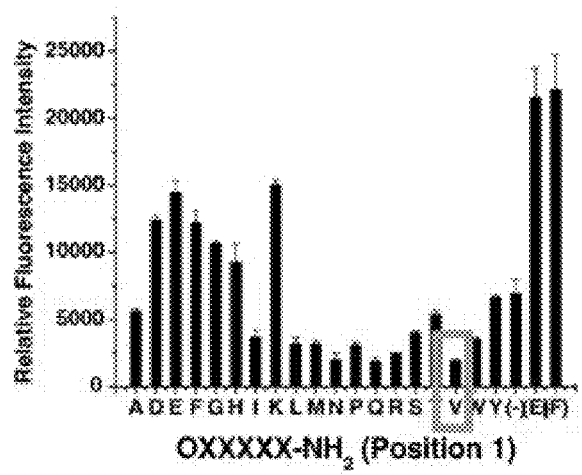
FIG. 3A illustrates results for a peptide with an amino acid located at Position 1.
Figure 3B:
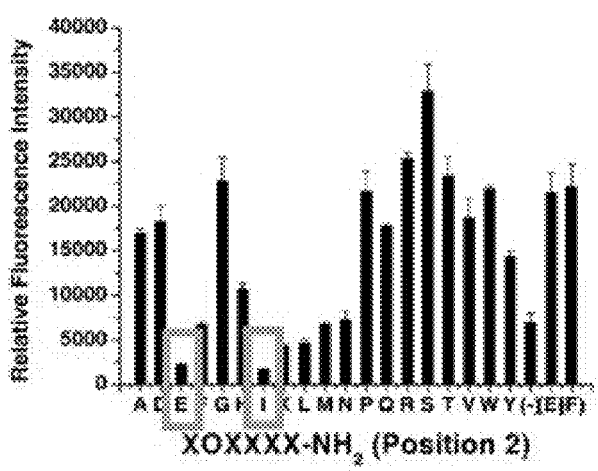
FIG. 3B illustrates results for a peptide with an amino acid located at Position 2.
Figure 3C:
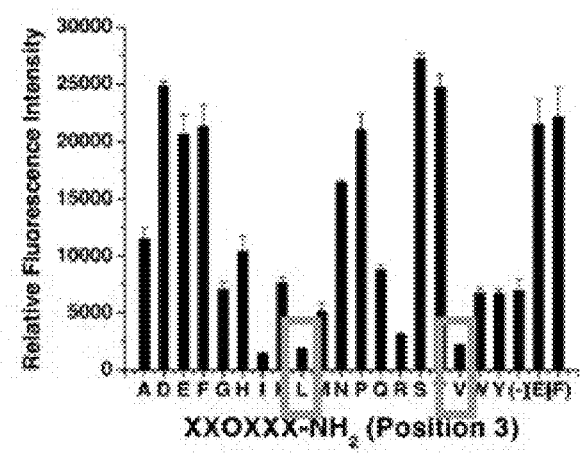
FIG. 3C illustrates results for a peptide with an amino acid located at Position 3.
Figure 3D:
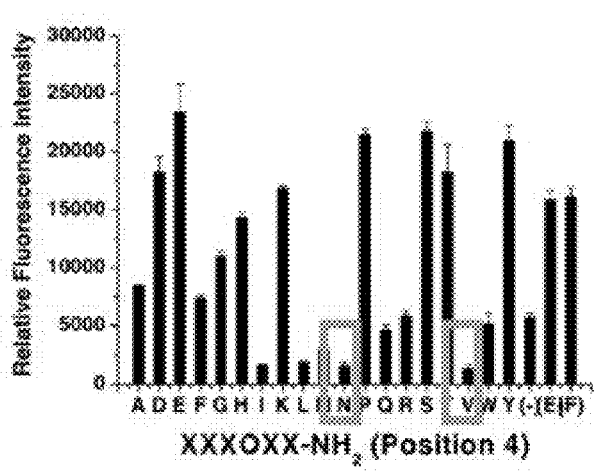
FIG. 3D illustrates results for a peptide with an amino acid located at Position 4.
Figure 3E:
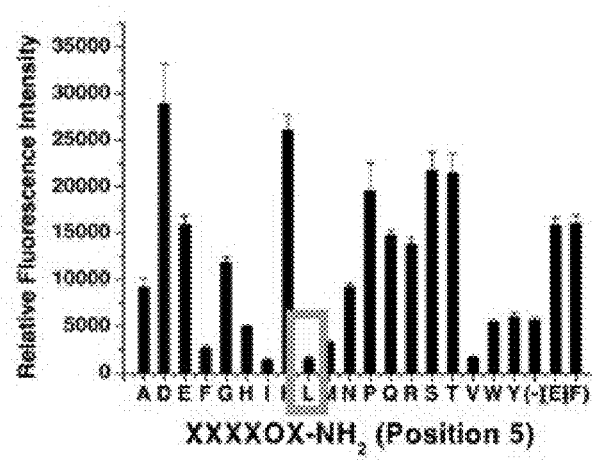
FIG. 3E illustrates results for a peptide with an amino acid located at Position 5.
Figure 3F:
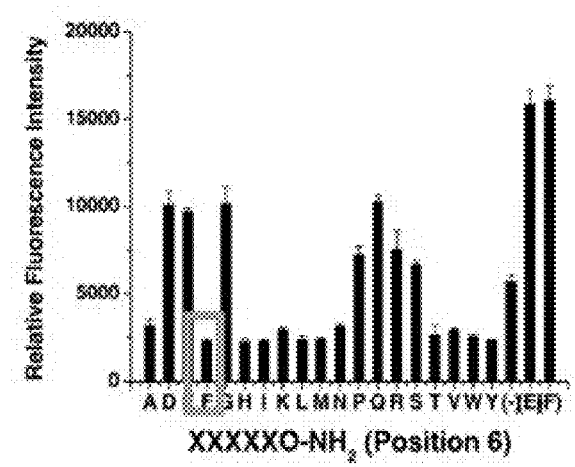
FIG. 3F illustrates results for a peptide with an amino acid located at Position 6.
Figure 4:
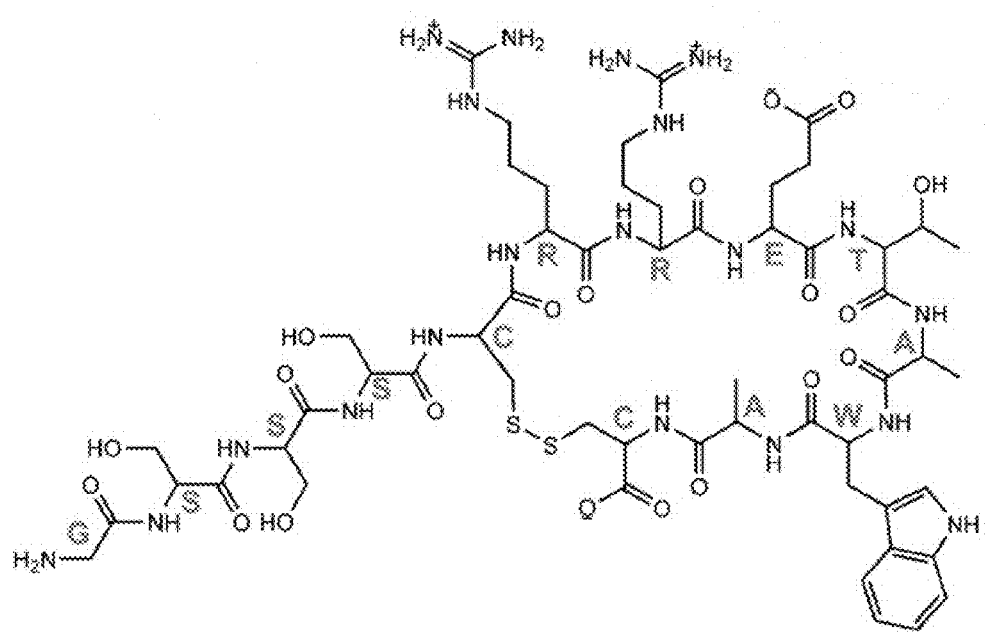
FIG. 4 shows the structure of CRRETAWAC (SEQ ID NO:1)-containing cyclic peptide for use in modification of ePTFE. This peptide allowed high EC binding through $\alpha_5\beta_1$ integrin and showed low platelet adhesion.
Figure 5A:
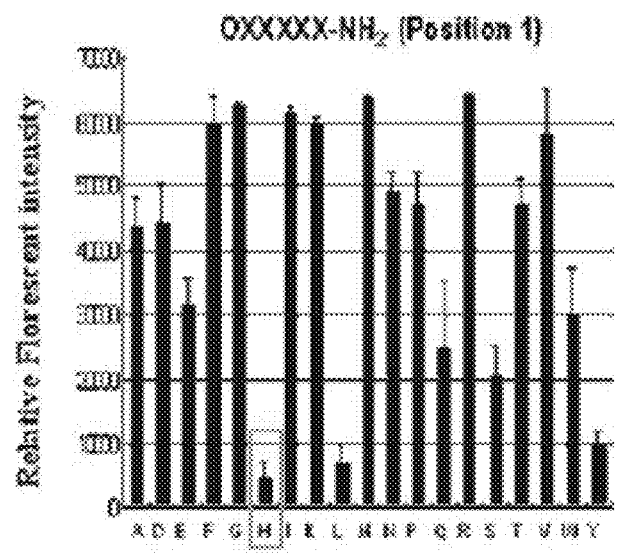
FIG. 5A illustrates results for a peptide with an amino acid located at Position 1.
Figure 5B:
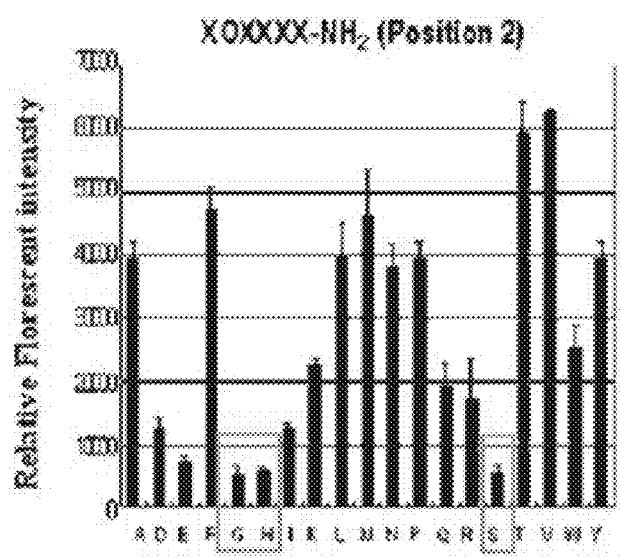
FIG. 5B illustrates results for a peptide with an amino acid located at Position 2.
Figure 5C:
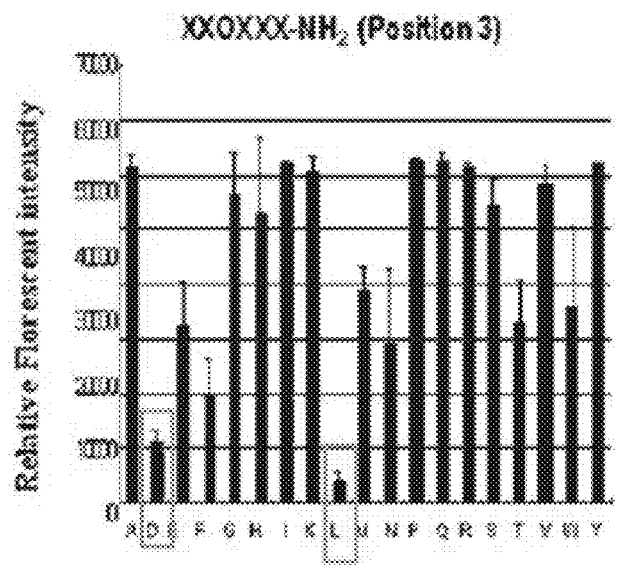
FIG. 5C illustrates results for a peptide with an amino acid located at Position 3.
Figure 5D:
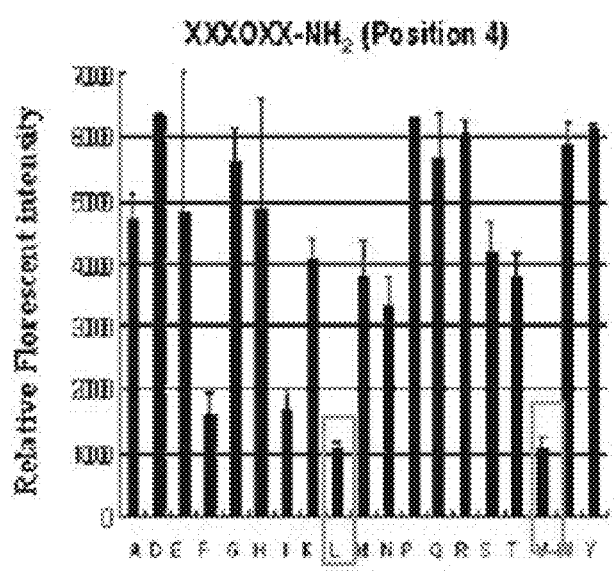
FIG. 5D illustrates results for a peptide with an amino acid located at Position 4.
Figure 5E:
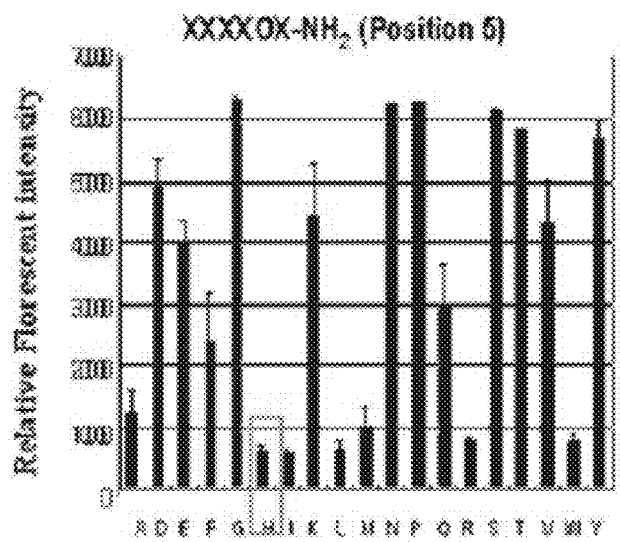
FIG. 5E illustrates results for a peptide with an amino acid located at Position 5.
Figure 5F:
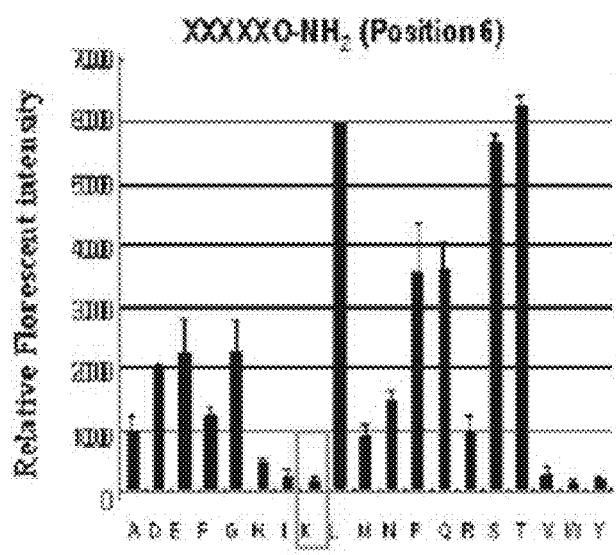
FIG. 5F illustrates results for a peptide with an amino acid located at Position 6.

Results:

ECFCs were able to form monolayer and maintain cobble stone morphology on RGDS (SEQ ID NO:3), CRRETAWAC (SEQ ID NO:1) and PR_b (SEQ ID NO: 8), grafted hydrogels, but not on REDV (SEQ ID NO:2), YIGSRG (SEQ ID NO:4), and P11 (SEQ ID NO: 11). Rolling velocity of ECFCs was shown to relate to shear rates and adhesion material surface. ECFC rolling velocities increased as shear rates increased up to 120 s$^{-1}$ (FIG. 1). All bioactive peptides supported ECFC rolling as the velocities were well below the cutoff for rolling velocity. ECFC rolling velocity was found to be significantly lower on REDV (SEQ ID NO:2)-grafted hydrogels. This suggests that $\alpha_4\beta_1$ integrins may be important in ECFC rolling. ECFC capture events were only observed on hydrogels grafted with $\alpha_5\beta_1$ binding peptides, CRRETAWAC (SEQ ID NO:1) and PRb (SEQ ID NO: 8), at 20 s$^{-1}$. Combination of REDV (SEQ ID NO:2) and CRRETAWAC (SEQ ID NO:1) have significantly increased the capture rate of ECFC under shear (FIG. 2).

Conclusions:

All tested bioactive peptides supported ECFC rolling, whereas PEG-DA alone and RGES (SEQ ID NO:5) did not. PEG-DA was shown to be a viable "blank slate" base material for testing the ability of grafted ligands, including PEG-peptides, to interact with rolling ECFCs. Results demonstrated the ability of $\alpha_4\beta_1$ integrin-specific peptide REDV (SEQ ID NO:2) to significantly reduce ECFC rolling velocity as compared to other tested peptide sequences. Capture on CRRETAWAC (SEQ ID NO:1) and PRb (SEQ ID NO: 8), suggests that $\alpha_5\beta_1$, rather than $\alpha_v\beta_3$, is the major integrin that is responsible for ECFC capture under shear. CRRETAWAC (SEQ ID NO:1) was found to be superior in capturing rolling ECFCs under shear, and this effect was enhanced by the combination of REDV (SEQ ID NO:2). Results of this study could be applied in the design of biomaterials for stent coating and vascular grafts to enhance endothelialization and improve EPC strength of adhesion under shear.

Example 2: Identification of Novel Peptides for Slower ECFC Rolling and Enhanced ECFC Capture Ability Introduction Pepbank is a useful text mining tool that was developed to identify peptide sequences in MEDLINE abstracts and two public sources ASPD and UniProt. With this searching tool, peptides that are relevant to target integrins can be researched. When both integrins $\alpha_5\beta_1$ and $\alpha_v\beta_3$ are blocked, EPC adhesion was significantly reduced. Therefore, it is important to identify peptides that bind to these integrins. Initially, 47 and 88 hits were obtained for $\alpha_5\beta_1$ and $\alpha_v\beta_3$, respectively. Almost all RGD- and PHSRN (SEQ ID NO:9)-containing peptides were excluded from the results since RGD is a ubiquitous peptide while PHSRN (SEQ ID NO:9) is a well-known synergistic peptide that works together with RGD. For peptides that bind $\alpha_5\beta_1$, VILVLF (A5-1; SEQ ID NO:21), and —(C16)2-Glu-C2-KSSPHSRNSGSGSGSG-GRGDSP (SEQ ID NO:8) (PR_b) were selected for further testing. HSDVHK (SEQ ID NO:11) (P11) and NCKHQCT-CIDGAVGCIPLCP (SEQ ID NO:12) (V2) were selected for $\alpha_v\beta_3$ testing.

Materials and Methods

Peptide Synthesis

VILVLFG (SEQ ID NO:15) was synthesized using standard procedures. Mass spectrometry was used to confirm the synthesis.

Some alterations in the sequence of the peptide and extra reactions were involved in the testing of CRRETAWAC (SEQ ID NO:1), compared to work previously conducted. In prior studies, the peptide sequence GSSS (SEQ ID NO:16) was added at the N-terminus of CRRETAWAC (SEQ ID NO:1) to extend the peptide further away from the substrate interface. In this project, all peptides were coupled to the acryloyl-PEG that serves as the spacer arm, so GSSS may not be necessary. Therefore, the original peptide CRRETAWAC (SEQ ID NO:1) was synthesized for testing in the present work, instead of GSSSCRRETAWAC (SEQ ID NO:7). In order to create the disulfide bridge to form the cyclic CRRETAWAC (SEQ ID NO:1) peptide, Fmoc-Sacetaminomethyl-L-cysteine (Fmoc-Cys(Acm)) was used during the peptide synthesis because the Acm protection group is stable during TFA cleavage. The disulfide bridge can be formed subsequent to cleavage with iodine oxidation as suggested by aapptec. The peptide was dissolved in 2 mg/mL of 50% acetic acid. Then the peptide solution was added into 50 mL of 0.1 M iodine solution in acetic acid. The mixture was then stirred until the yellow color persists. Aqueous ascorbic acid was added drop-wise to quench the excess iodine until the mixture is colorless. The mixture was placed in rotavap to concentrate by evaporation to approximately one third of the original volume. Mass spectrometry was used to confirm the production of the peptide and the cyclic CRRETAWACG (SEQ ID NO:17) should have a molecular weight of 1150 g/mol. However, the cyclized CRRETAWACG (SEQ ID NO:17) (1150 g/mol) was only the minor product whereas the major products were shown to be 1221 g/mol and 1292 g/mol which correspond to the peptide with a single and double Acm protection groups present. After extra iodine oxidation procedures were followed, similar results were obtained. Therefore, the peptide CRRETAWAC (SEQ ID NO:1) (instead of CRRETAWACG (SEQ ID NO:17)) was purchased from American Peptide with >95% purity. Formation of disulfide bonds between the cysteine residues was completed by manufacturer as requested.

Regarding to the original PRb peptide, the C16 hydrophobic tail, glutamic acid tail connector, and the —C2-tail spacer will be discarded to reduce peptide synthesis complexity. As a result, PHSRNSGSGSGSGSGRGDSG (SEQ ID NO:18) (PRb) was synthesized under standard procedures. Mass spectrometry was used to confirm the synthesis.

HSDVHKG (SEQ ID NO:19) was synthesized under standard procedures. Mass spectrometry was used to confirm the synthesis.

NCKHQCTCIDGAVGCIPLCPG (SEQ ID NO:20) (V2) was synthesized under standard procedures, which in this sequence identifier includes the G residue from which the peptide was built. Mass spectrometry was used to confirm the synthesis. However, the peptide was not readily to be dissolved in aqueous injection solution for mass spectrometry analysis. Furthermore, many unexpected by-products were present. Therefore, the V2 peptide was excluded in this study due to the inability to accurately synthesize the peptide.

PEG-Peptide Conjugation and Confirmation Through Mass Spectrometry

CRRETAWAC (SEQ ID NO:1), PRb (SEQ ID NO:18), and HSDVHKG (SEQ ID NO:19) were conjugated to PEG as described in Example 1. Mass spectrometry was used to confirm the conjugation. While attempting with the PEG-peptide conjugation under organic solvents as suggested by the existing art, A5-1 peptide precipitated immediately after the addition of DIPEA, which acts as a base catalyst. Therefore, A5-1 was excluded in this study due to the inability to conjugate to acryloyl-PEG for grafting.

Results and Discussion

Adhesion of ECFCs on Novel Peptide-Grafted PEG Hydrogels

Figure 6A:
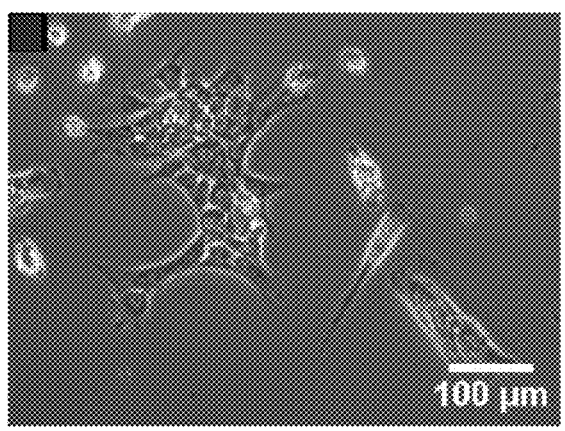
FIG. 6(A-C) shows adhesion of ECFCs on novel peptides-grafted PEG hydrogels after 24 hours. ECFC adhesion on (A) CRRETAWAC (SEQ ID NO:1)-(B) PRb (SEQ ID NO: 8), —(C) P11 (SEQ ID NO: 11)-grafted PEG hydrogels.
Figure 6B:
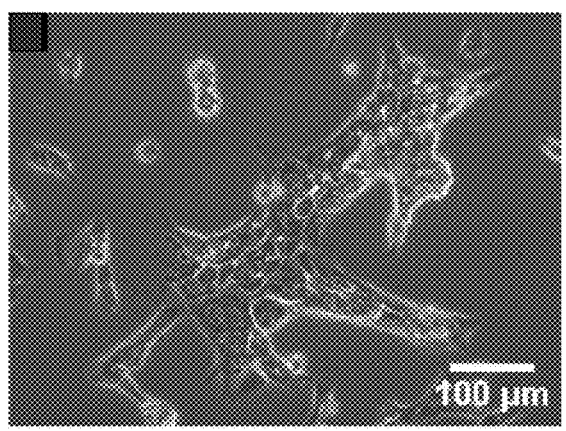
Figure 6C:
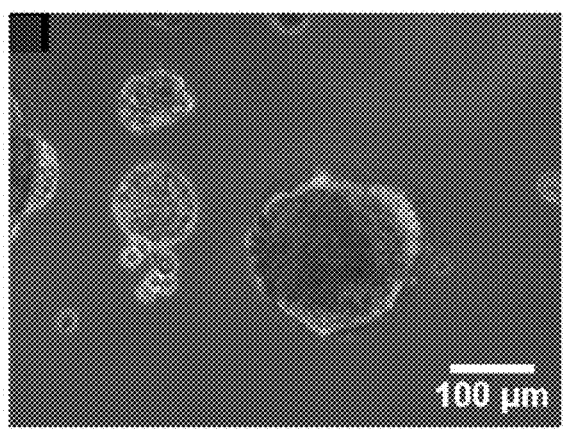

Adhesion of ECFCs on CRRETAWAC (SEQ ID NO:1)-, PRb (SEQ ID NO:18)-, P11 (SEQ ID NO: 11)-grafted hydrogels was first accessed. Both CRRETAWAC (SEQ ID NO:1) and PRb supported ECFC adhesion and spreading. ECFCs were also able to form a monolayer and maintain their cobble stone morphology (as shown in FIGS. 6A and 6B). However, P11 (SEQ ID NO: 11)-grafted hydrogels were only able to support ECFC adhesion, but not spreading (FIG. 6C). On P11-grafted hydrogels, ECFCs aggregated to form adherent cell clumps. This suggests that although P11 (SEQ ID NO: 11) was found to have high specificity for $\alpha_v\beta_3$, it may not support regular cellular activities other than cell adhesion. Without the ability to support cell spreading and the formation of monolayer, P11 alone could not support ECFC endothelialization which is critical for healing damaged and diseased blood vessels.

Similar ECFC Rolling Velocity Exhibited by Novel Peptides Comparing to RGDS (SEQ ID NO:3)

Figures 7A, 7B:
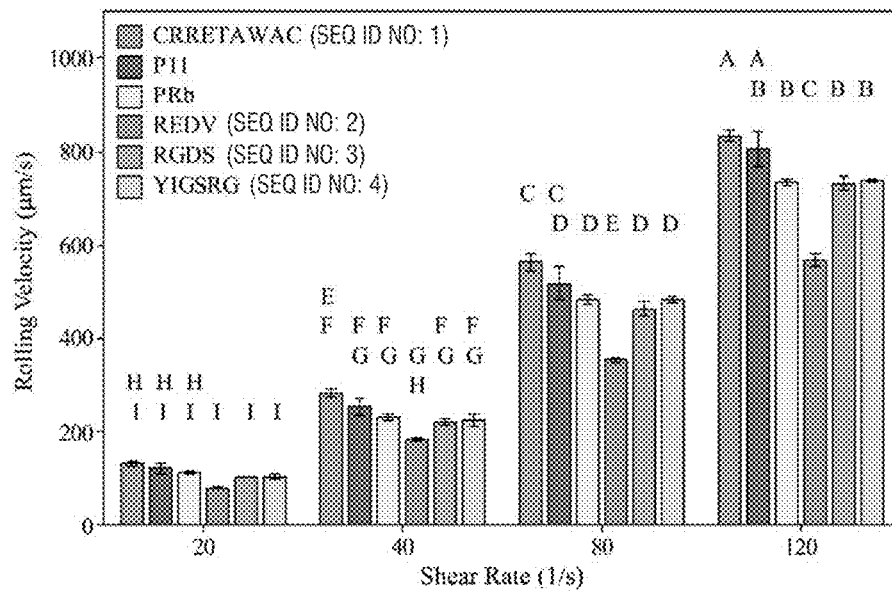
FIG. 7A provides a graphical representation of shear rate, while FIG. 7B provides the corresponding data in table format.
Figure 8:
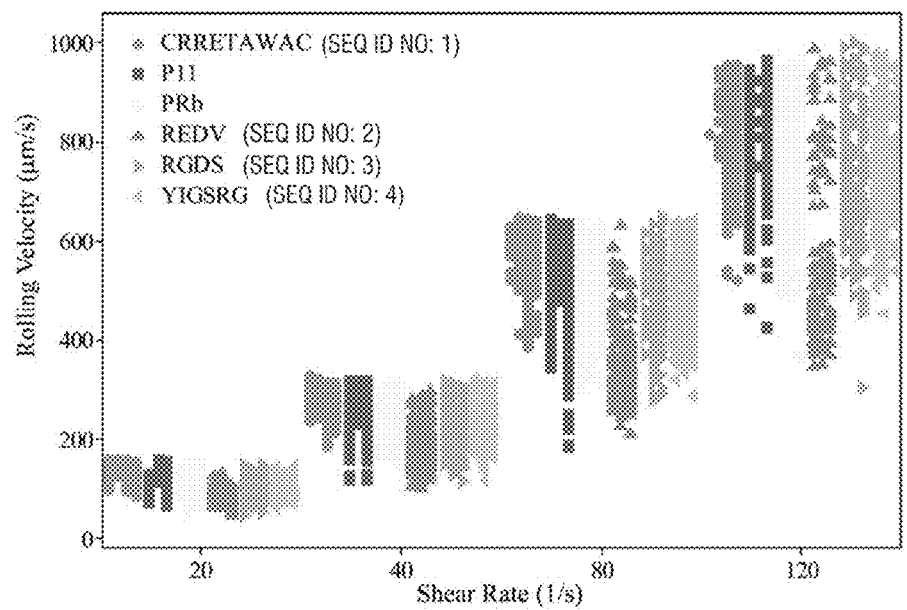
FIG. 8 shows the distribution of rolling velocities for rolled ECFCs on the peptide-grafted hydrogels at each tested shear rate. Each marker represents one tracked cell. Separately prepared peptide-grafted hydrogels were used for each trial.

ECFC rolling was performed on novel peptide-grafted hydrogels and the results were compared to RGDS (SEQ ID NO:3), REDV (SEQ ID NO:2), and YIGSRG (SEQ ID NO:4)-grafted hydrogels (FIG. 7, Table 2, and FIG. 8). All novel peptides supported ECFC rolling as the velocities were well below the cutoff for rolling velocity. Regarding the novel peptide, P11 showed the lowest rolling velocity whereas CRRETAWAC (SEQ ID NO:1) showed the highest rolling velocity at all shear rates. Comparing to RGDS (SEQ ID NO:3) and YIGSRG (SEQ ID NO:4), both P11 (SEQ ID NO: 11) and PRb (SEQ ID NO:18) showed similar rolling velocities and CRRETAWAC (SEQ ID NO:1) showed significantly higher rolling velocities at all shear rates. ECFC rolling velocities of all three novel peptides were significantly higher than REDV (SEQ ID NO:2) at 40 $s^{-1}$, 80 $s^{-1}$, and 120 $s^{-1}$. Some ECFC capture events were observed on CRRETAWAC (SEQ ID NO:1) and PRb-grafted hydrogels at 20 $s^{-1}$. In summary, the all tested novel peptides support ECFC rolling.

TABLE 2

| Peptide | Shear Rate (1/s) | | | |
| --- | --- | --- | --- | --- |
| | 20 | 40 | 80 | 120 |
| CRRETAWAC (SEQ ID NO: 1) | 131.6 ± 16.3 | 278.4 ± 28.6 | 550.6 ± 64.1 | 828.4 ± 82.7 |
| P11 (SEQ ID NO: 11) | 127.5 ± 18.4 | 251.0 ± 41.2 | 508.0 ± 86.5 | 787.6 ± 102.1 |
| PRb (SEQ ID NO: 18) | 110.3 ± 17.7 | 235.0 ± 36.1 | 485.7 ± 67.5 | 735.1 ± 102.6 |
| REDV (SEQ ID NO: 2) | 78.6 ± 15.8 | 183.3 ± 43.4 | 353.8 ± 82.0 | 564.3 ± 177.0 |
| RGDS (SEQ ID NO: 3) | 102.2 ± 20.1 | 218.7 ± 42.4 | 455.8 ± 86.7 | 739.7 ± 121.9 |
| YIGSRG (SEQ ID NO: 4) | 103.2 ± 18.9 | 223.2 ± 38.0 | 487.6 ± 72.5 | 737.0 ± 107.9 |

ECFC Capture on CRRETAWAC (SEQ ID NO:1)- and PRb (SEQ ID NO:18)-Grafted Hydrogels Cell capture events were consistently observed on CRRETAWAC (SEQ ID NO:1)- and PRb (SEQ ID NO:18)-grafted hydrogels at 20 $s^{-1}$. Number of captured cells were counted and normalized to the total number of cells interacted with each hydrogel surface. During each of the 2 min recordings, 3.74%±1.0% of ECFCs were captured on CRRETAWAC (SEQ ID NO:1)-grafted hydrogels and 1.14%±0.2% of ECFCs were captured on PRb-grafted hydrogels FIG. 9. Since both of these novel peptides are specific for the integrin $\alpha_5\beta_1$, the result of this study strongly supports that $\alpha_5\beta_1$ is responsible for cell capture. This is in agreement with previous studies that have suggested that initial capture of EPCs is directly dependent on integrin $\alpha_5\beta_1$.

Figure 9:
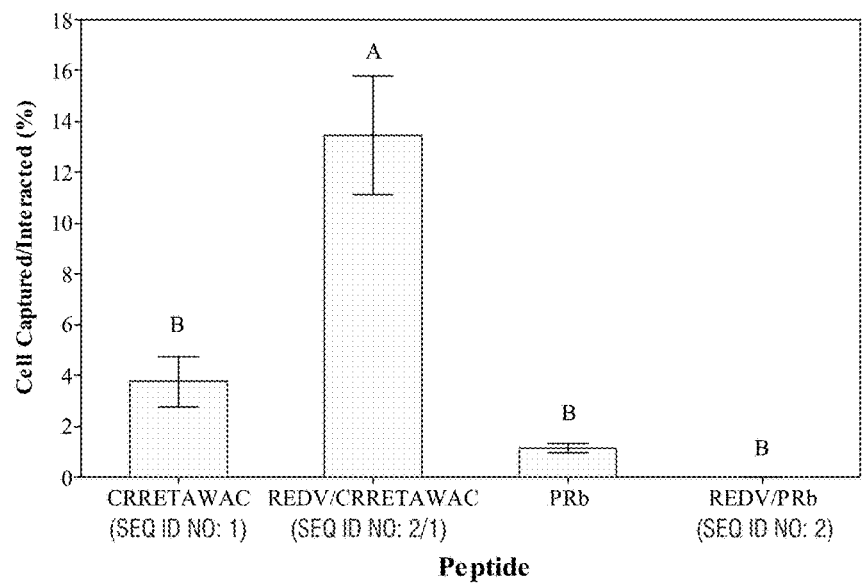
FIG. 9 shows the number of ECFC captured between novel peptides and known ECM peptides. Conditions that do not share the same letter are significantly different (p<0.05) based on Tukey's test. Data represent mean±SD (n=3).

Increased ECFC Capture on REDV (SEQ ID NO:2)/CRRETAWAC (SEQ ID NO:1)-Grafted Hydrogels To further evaluate the potential use of CRRETAWAC (SEQ ID NO:1) and PRb in the ECFC capture for endothelialization, ECFC rolling on hydrogels that were grafted with combinations of CRRETAWAC (SEQ ID NO:1) or PRb (SEQ ID NO:18) with REDV (SEQ ID NO:2) was assessed. In order to maintain consistent grafting of peptides, a final concentrations of 0.7 µmol/mL of equal molar mixtures of acryloyl-PEG-peptides precursors were grafted onto the surface of PEG hydrogels. Hydrogels grafted with REDV (SEQ ID NO:2)/CRRETAWAC (SEQ ID NO:1) combination (0.35 µmol/mL of REDV (SEQ ID NO:2)/0.35 µmol/mL of CRRETAWAC (SEQ ID NO:1)) had significantly increased ECFC capture of 13.4%±2.3% as compared to CRRETAWAC (SEQ ID NO:1) alone (FIG. 9). This increased ECFC capture may be due to the contribution from REDV (SEQ ID NO:2) which has shown that it significantly reduces the rolling velocity. This theory was supported by the observation of lower rolling velocity on REDV (SEQ ID NO:2)/CRRETAWAC (SEQ ID NO:1)-grafted hydrogels (FIG. 10), although no significant difference was found between the rolling velocities on CRRETAWAC (SEQ ID NO:1) and REDV (SEQ ID NO:2)/CRRETAWAC (SEQ ID NO:1) at all tested shear rates.

No ECFC Capture on REDV (SEQ ID NO:2)/PRb-Grafted Hydrogels

Figure 10:
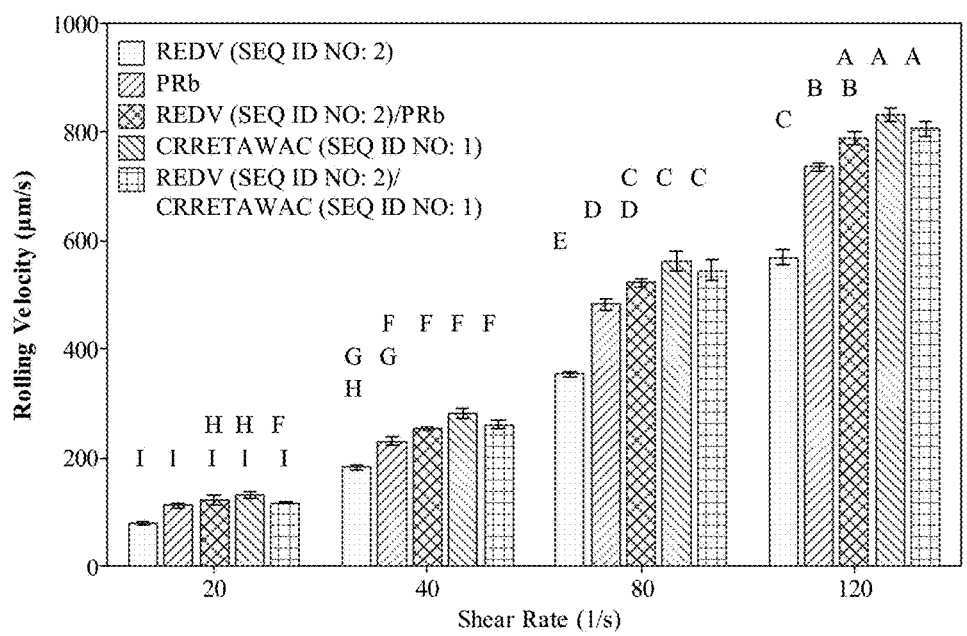
FIG. 10 shows rolling velocity between novel peptides, known ECM peptides, and combinations thereof. Conditions that do not share the same letter are significantly different (p<0.05) from Tukey's test. Data represent mean±SD (n=3).
Figure 11:
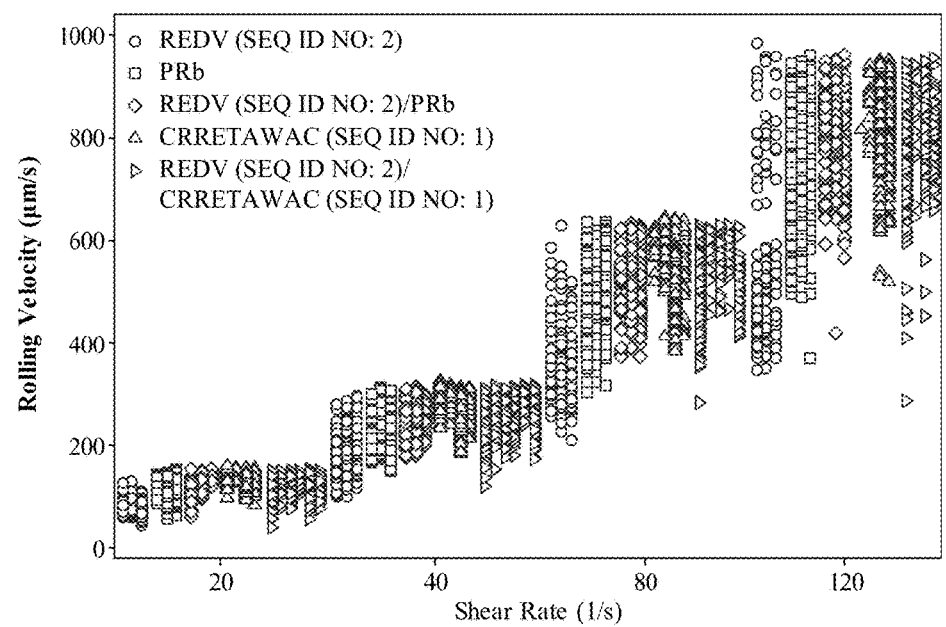
FIG. 11 shows the distribution of rolling velocities for rolled ECFCs on the peptide-grafted hydrogels at each tested shear rate. Each marker represents one tracked cell. Separately prepared peptide-grafted hydrogels were used for each trial.

As REDV (SEQ ID NO:2) has a significantly positive effect on enhancing the ability of CRRETAWAC (SEQ ID NO:1) to support ECFC capture, it has a negative effect on PRb's (SEQ ID NO:18) ability to support ECFC capture (FIG. 9). The implementation of REDV (SEQ ID NO:2) in combination with PRb has completely eliminated PRb's capability for ECFC capture (from 1.14%±0.2% to 0%). This unforeseen result was probably due to the significant difference in length of the two peptides. Unlike CRRETAWAC (SEQ ID NO:1), PRb has no Cys that forms internal disulfide bridge, so it is considered as a linear peptide. While REDV (SEQ ID NO:2) has four amino acids, PRb has 20 amino acids, which is five times longer than REDV (SEQ ID NO:2). The much longer PRb may have shielded the shorter REDV (SEQ ID NO:2) which restricted the access of integrin $\alpha_4\beta_1$ on ECFCs to REDV (SEQ ID NO:2). This is also supported by the increase in ECFC rolling velocity on REDV (SEQ ID NO:2)/PRb-grafted hydrogels compared to PRb alone as shown in FIG. 10 and FIG. 11.

Conclusions

Novel peptides were selected to evaluate their capability in slowing and capturing EPCs. Pepbank was used to identify peptides that have high affinity and/or selectivity for the integrins $\alpha_5\beta_1$ and $\alpha_v\beta_3$. Although these peptides have shown great promise in cell adhesion, their performance in cell rolling and capture under shear is yet to be evaluated. Although five peptides were identified, three were assessed due to the success in synthesis and conjugation to acryloyl-PEG. Assessment of CRRETAWAC (SEQ ID NO:1) and PRb (SEQ ID NO: 8 or 18) showed that $\alpha_5\beta_1$ is the major integrin that is responsible for ECFC capture under shear. CRRETAWAC (SEQ ID NO:1) was found to be superior in capturing rolling ECFCs under shear, and this effect was enhanced by the implementation of REDV (SEQ ID NO:2). PRb also has potential in capturing ECFCs, although its capturing ability was not observed when implementing REDV (SEQ ID NO:2). This illustrates the importance of the peptide length in biomaterial design.

Example 3: ECFC Rolling on Hydrogels

Figure 12:
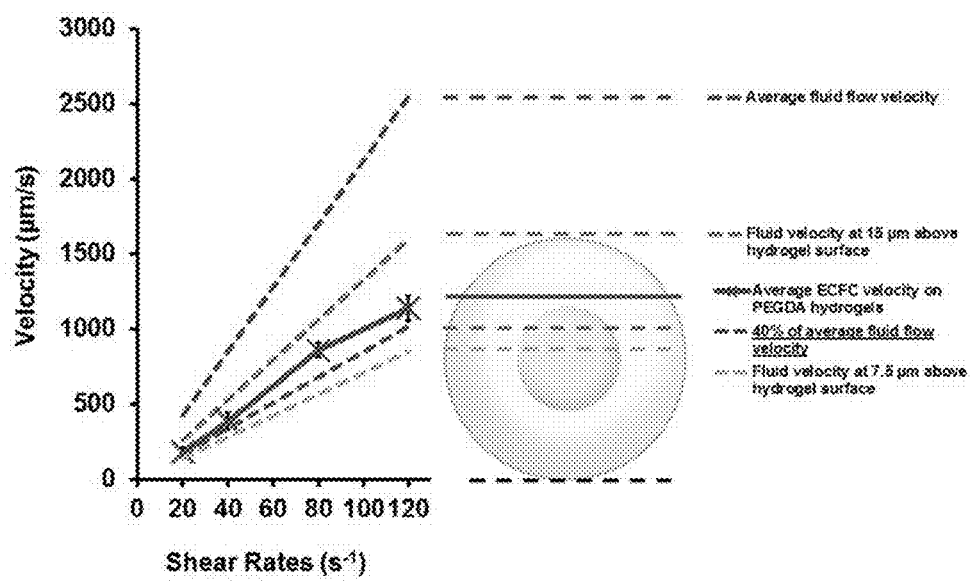
FIG. 12 shows a comparison between calculated fluid velocities and ECFC velocity. The velocity of ECFCs on the surface of PEG hydrogels was less than the calculated fluid velocity at approximately one cell diameter (15 µm) and greater than the calculated fluid velocity at approximately one cell radius (7.5 µm) above the hydrogel surface. Data represent mean±SD (n=3). Therefore, to eliminate any ECFCs that might be non-specifically interacting with the PEG hydrogel surface, the cutoff for identification of rolling cells was set at 40% of the average fluid velocity.

To identify whether a cell is rolling, the upper velocity cutoff was determined by flowing ECFCs across the surface of control PEG hydrogels at different shear rates. Using video recordings, ECFC rotation on the focal plane of PEG hydrogels was observed. As shown in FIG. 12, cell tracking showed that ECFCs' average velocity on PEG hydrogels fell between estimated fluid flow velocity at a distance of approximately one cell diameter (i.e. 15 µm, the average diameter of ECFCs in suspension) above the hydrogel surface and the estimated fluid flow velocity at a distance of approximately one cell radius (i.e. 7.5 µm) above the hydrogel surface. Therefore, based on these experiments, 40% of average fluid flow velocity was used as the cutoff velocity for cell rolling as is shown in FIG. 12.

Figure 13A:
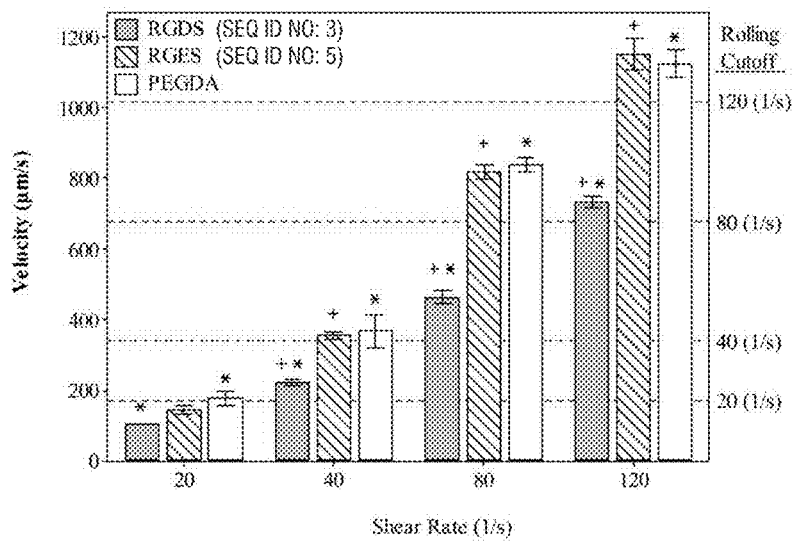
FIG. 13(A-C) shows grafting PEG hydrogels with RGDS (SEQ ID NO:3) significantly slowed ECFC velocity. (A) The ECFCs velocity on RGES (SEQ ID NO:5)-grafted hydrogels was similar to the velocity on ungrafted PEGDA hydrogels, while ECFC rolling velocity on RGDS (SEQ ID NO:3)-grafted hydrogel showed a significant decrease compared to RGES (SEQ ID NO:5)-grafted and PEGDA hydrogels at all shear rates. Data represent mean±SD (n=3). (*p<0.05 between RGDS (SEQ ID NO:3)-grafted hydrogels and ungrafted PEGDA hydrogels. +p<0.05 between RGDS (SEQ ID NO:3)- and RGES (SEQ ID NO:5)-grafted hydrogels). (B,C) Instantaneous velocity, average rolling velocity and 40% of average fluid velocity of representative ECFCs on PEG, PEG-RGES (SEQ ID NO:5), and PEG-RGDS (SEQ ID NO:3) hydrogels at shear rates of 80 s$^{-1}$ and 120 s$^{-1}$, respectively.
Figure 13B:
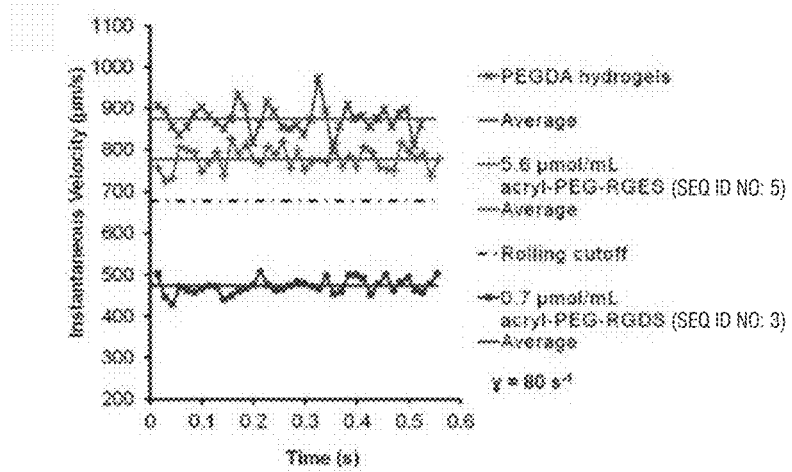
Figure 13C:
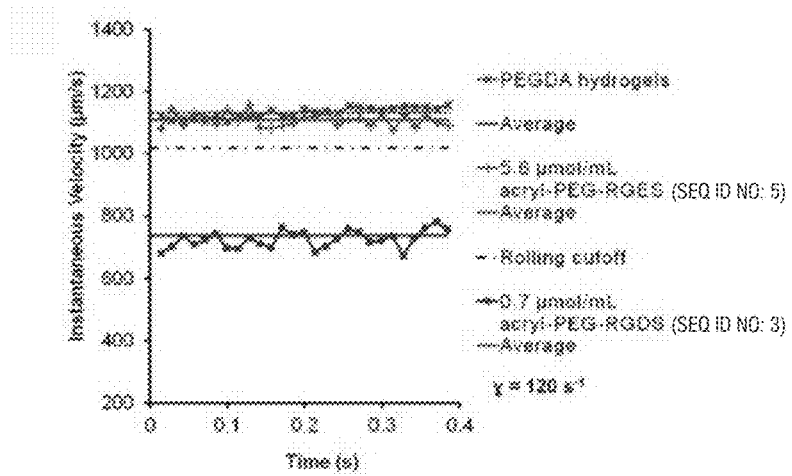
Figure 14A:
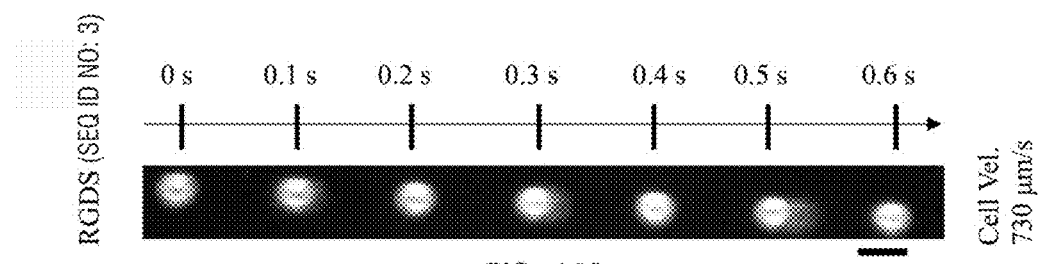
FIG. 14(A-C) shows a series of extracted frames following a representative ECFC through the flow chamber on (A) PEG, (B) 5.6 µmol/mL RGES (SEQ ID NO:5)-grafted, (C) 0.7 µmol/mL RGDS (SEQ ID NO:3)-grafted hydrogels. Scale bar=30 µm.
Figure 14B:
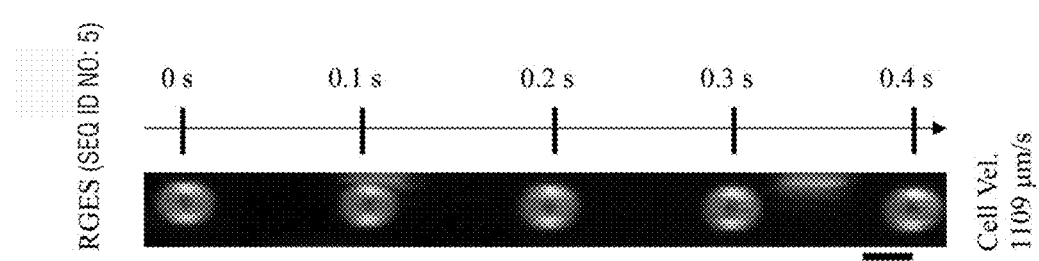
Figure 14C:
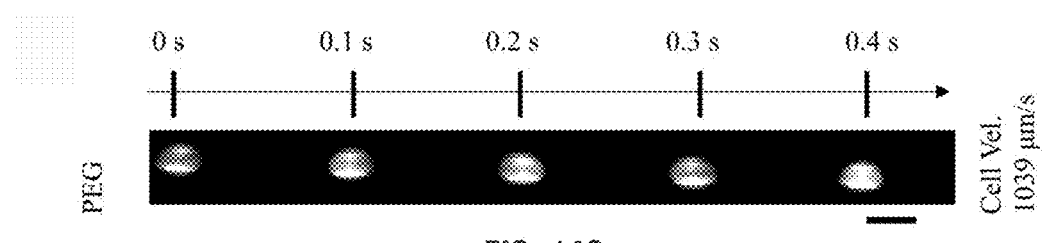

ECFC rolling on RGDS (SEQ ID NO:3)-grafted hydrogels was performed and compared to both PEG hydrogels and RGES (SEQ ID NO:5)-grafted hydrogels. RGDS (SEQ ID NO:3) is a ubiquitous cell adhesion peptide, whereas RGES (SEQ ID NO:5) does not support cell adhesion and served as a control peptide. Velocities of ECFCs on RGES (SEQ ID NO:5) showed no significant difference as compared to control PEGDA hydrogels. On the other hand, velocities of ECFCs on RGDS (SEQ ID NO:3)-grafted hydrogels were significantly decreased as compared to ECFC velocities on RGES (SEQ ID NO:5)-grafted hydrogels at all shear rates. As shown in FIG. 13A, the rolling velocities of ECFCs on RGDS (SEQ ID NO:3)-grafted hydrogels were 103±3 µm/s, 223±14 µm/s, 469±38 µm/s, and 741±28 µm/s at 20 $s^{-1}$, 40 $s^{-1}$, 80 $s^{-1}$, and 120 $s^{-1}$, respectively. Representative traces of individual cells' instantaneous velocities on RGDS (SEQ ID NO:3)-grafted, RGES (SEQ ID NO:5)-grafted, and control PEGDA surfaces are shown in FIGS. 13B and C. For each tested surface, a series of extracted frames following a representative ECFC moving through the flow chamber is presented in FIG. 14. Some ECFC capture events were observed on RGDS (SEQ ID NO:3)-grafted hydrogels at 20 $s^{-1}$; the total number of capture events at this shear rate was far less than the number of rolling cells, however, and, therefore, insufficient for analysis (data not shown). In summary, the RGDS (SEQ ID NO:3)-grafted hydrogels supported ECFC rolling at all shear rates whereas RGES (SEQ ID NO:5)-grafted hydrogels did not support ECFC rolling. Specific transient binding between ECFCs and RGDS (SEQ ID NO:3) was demonstrated.

Figure 15A:
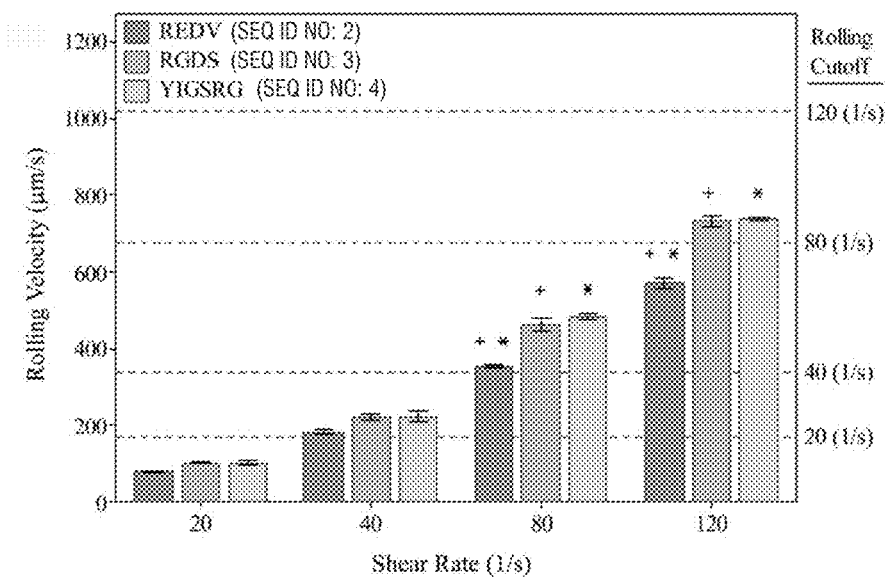
FIG. 15(A-C) shows a comparison of ECFC rolling on REDV (SEQ ID NO:2)-, RGDS (SEQ ID NO:3)-, and YIGSRG (SEQ ID NO:4)-grafted hydrogels. A) ECFC rolling velocity was lower on REDV (SEQ ID NO:2)-grafted hydrogels as compared to RGDS (SEQ ID NO:3)-grafted hydrogels and YIGSRG (SEQ ID NO:4)-grafted hydrogels at all shear rates. Data represent mean±SD (n=3). (* and +p<0.05 within groups of 80 s$^{-1}$ and 120 s$^{-1}$). B,C) Instantaneous velocity, average rolling velocity and 40% of average fluid velocity of representative ECFCs on REDV (SEQ ID NO:2)-, RGDS (SEQ ID NO:3)-, and YIGSRG (SEQ ID NO:4)-grafted hydrogels at 80 s$^{-1}$ and 120 s$^{-1}$, respectively.
Figure 15B:
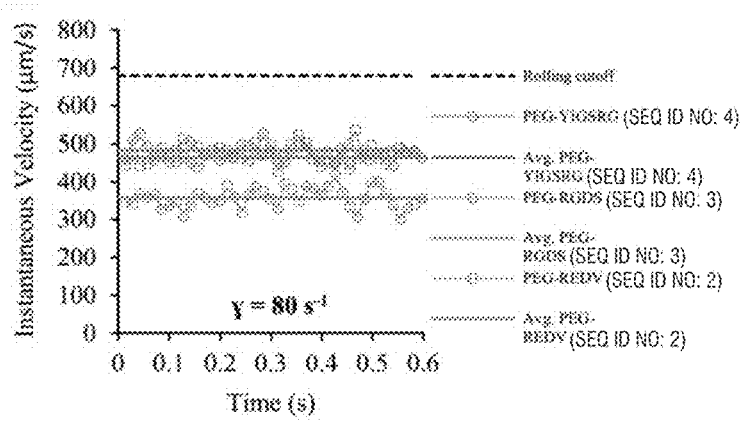
Figure 15C:
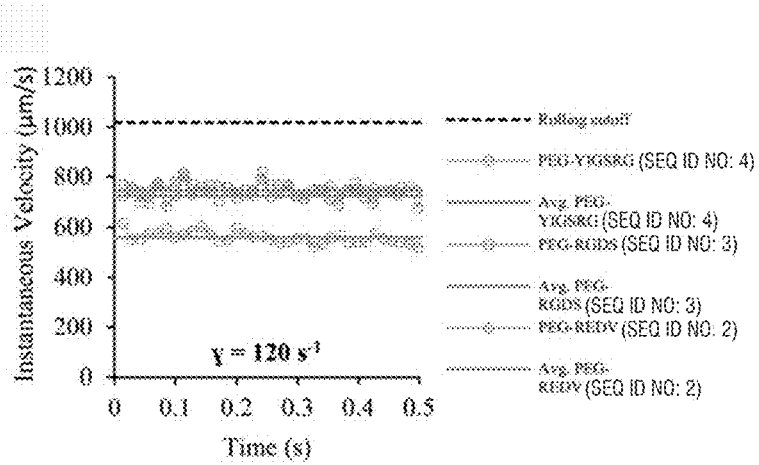
Figure 17:
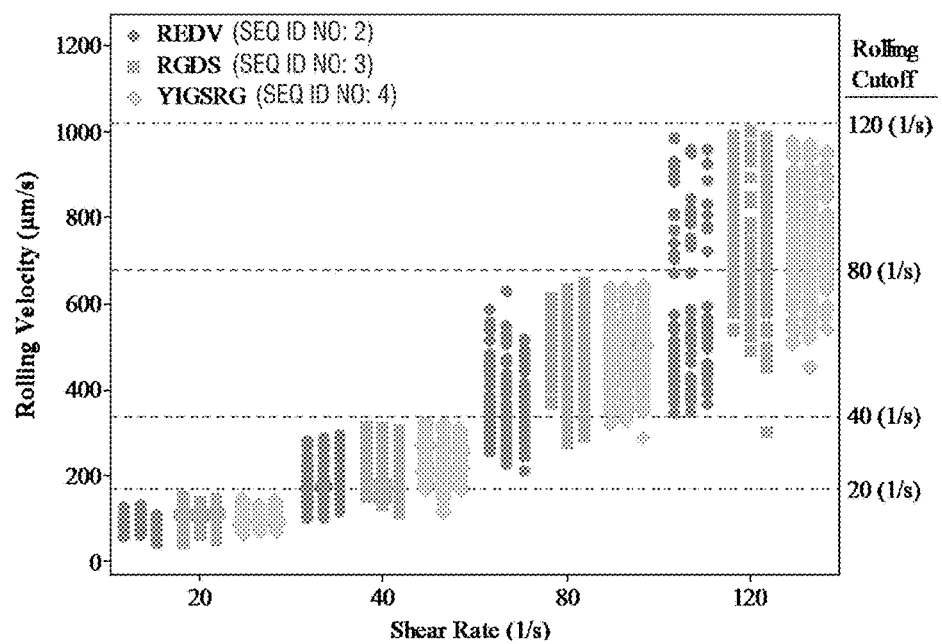
FIG. 17 shows the distribution of rolling velocities for tracked ECFCs on the peptide-grafted hydrogels at each tested shear rate. Each marker represents one tracked cell. Separately prepared peptide-grafted hydrogels were used for each trial. At shear rates of 80 s$^{-1}$ and 120 s$^{-1}$, more cells are grouped at the lower rolling velocities for REDV (SEQ ID NO:2)-grafted hydrogels than for RGDS (SEQ ID NO:3)- and YIGSRG (SEQ ID NO:4)-grafted hydrogels.

In addition to PEG-RGDS (SEQ ID NO:3), PEG-YIGSRG (SEQ ID NO:4) and PEG-REDV (SEQ ID NO:2) grafted hydrogels also supported ECFC rolling. YIGSRG (SEQ ID NO:4) and REDV (SEQ ID NO:2) are peptides known to preferentially interact with ECs. Rolling velocities on YIGSRG (SEQ ID NO:4) were similar to rolling velocities on RGDS (SEQ ID NO:3); specifically, the ECFC rolling velocities on PEG-YIGSRG (SEQ ID NO:4) grafted hydrogels were 102±9 µm $s^{-1}$, 223±22 µm $s^{-1}$, 484±12 µm $s^{-1}$, and 740±10 µm $s^{-1}$ at 20 $s^{-1}$, 40 $s^{-1}$, 80 $s^{-1}$, and 120 $s^{-1}$, respectively. Surprisingly, PEG-REDV (SEQ ID NO:2) grafted hydrogels reduced ECFC rolling velocities substantially more than either RGDS (SEQ ID NO:3)- or YIGSRG (SEQ ID NO:4)-grafted hydrogels (FIG. 15A). ECFC rolling velocities on PEG-REDV (SEQ ID NO:2) grafted hydrogels were 79±4 µm $s^{-1}$, 181±6 µm $s^{-1}$, 357±6 µm $s^{-1}$, and 560±15 µm $s^{-1}$ at 20 $s^{-1}$, 40 $s^{-1}$, 80 $s^{-1}$, and 120 $s^{-1}$, respectively ($p<0.05$ for shear rates at 80 $s^{-1}$, and 120 $s^{-1}$ compared to RGDS (SEQ ID NO:3) and YIGSRG (SEQ ID NO:4)). Representative plots of instantaneous rolling velocities for ECFCs that were tracked across the field of view at 80 $s^{-1}$ and 120 $s^{-1}$ are shown in FIGS. 15B and C. For each tested surface, a series of extracted frames following a representative ECFC moving through the flow chamber is presented in FIG. 16. To visualize the distribution of ECFC rolling velocities, each tracked ECFC is plotted against its rolling velocity in FIG. 17. To allow for better visualization of the data points and for visual comparison of ECFC velocity distributions between trials, cells are separated by trial, where each trial was performed using a separately prepared peptide-grafted hydrogel. At all shear rates, it can observed that on the REDV (SEQ ID NO:2)-grafted hydrogels a large number of ECFCs are grouped at lower rolling velocities with a more sparse distribution of ECFCs at higher rolling velocities, whereas on the RGDS (SEQ ID NO:3)- and YIGSRG (SEQ ID NO:4)-grafted hydrogels, the distribution of ECFCs is more even across all the observed rolling velocities, with more ECFCs tending to have higher rolling velocities. Upon closer examination, rolling velocities on REDV (SEQ ID NO:2)-grafted hydrogels at all shear rates were found to be significantly and positively skewed toward lower velocities at all shear rates. These results show that multiple peptides are able to support ECFC rolling, including RGDS (SEQ ID NO:3), YIGSRG (SEQ ID NO:4), and REDV (SEQ ID NO:2). In addition, RGDS (SEQ ID NO:3) and YIGSRG (SEQ ID NO:4) supported ECFCs rolling at similar velocities, whereas REDV (SEQ ID NO:2) slowed ECFC rolling velocity to a significantly greater extent. This significant decrease demonstrates that ECFC rolling velocity on the hydrogels depends on the particular grafted PEG-peptide and suggests that the integrin bound by REDV (SEQ ID NO:2), $α_4β_1$ may be important in ECFC rolling.

The above specification provides a description of various methods of generating three-dimensional cell cultures or tissues, compositions of the same, methods of use, treatment and diagnosing. Since many embodiments can be made without departing from the spirit and scope of the invention, the invention resides in the claims.

What is claimed is:

1. A composition for inducing endothelialization or vascularization, comprising:
   a substrate;
   at least one first peptide consisting of SEQ ID NO: 1 operatively linked to the surface of said substrate; and
   at least one second peptide consisting of SEQ ID NO: 2 operatively linked to the surface of said substrate.

2. The composition of claim 1, further comprising at least one additional peptide selected from the group consisting of SEQ ID NOs: 8, 11 and 18 and combinations thereof.

3. The composition of claim 1, wherein said substrate is selected from the group consisting of biomimetic material, a polymer, hydrogel, material suitable for use in a medical device or implant and decellularized extracellular matrix (dECM).

4. The composition of claim 1, wherein said substrate comprises a hydrogel.

5. The composition of claim 1, wherein said substrate comprises biomimetic material.

6. The composition of claim 5, wherein the substrate comprises decellularized extracellular matrix (dECM).

7. The composition of claim 1, wherein the molar ratio of the second peptide to the first peptide is between 3:1 and 1:3.

8. A method for capturing endothelial cells or supporting immature endothelial cells under physiological shear, the method comprising:
   providing a substrate that is operably linked to at least one first peptide consisting of SEQ ID NO: 1 and at least one second peptide consisting of SEQ ID NO: 2; and
   exposing said substrate to a source of endothelial cells.

9. The method of claim 8, wherein said endothelial cells are immature endothelial cells, endothelial progenitor cells, or pluripotent stem cell-derived endothelial cells.

10. The method of claim 8, wherein said substrate is further operably linked to at least one additional peptide selected from the group consisting of SEQ ID NOs: 8, 11 and 18 and combinations thereof.

11. The method of claim 8, further comprising subjecting the endothelial cells to physiologic shear in the presence of said substrate.

12. A method for producing an endothelial cell capture and support surface, the method comprising:
   providing a substrate;
   operably linking at least one first adhesion ligand peptide and at least one second adhesion ligand peptide to the surface of said substrate to produce a prepared surface, wherein said at least one first adhesion ligand peptide consists of SEQ ID NO: 1 and said at least one second adhesion ligand peptide consists of SEQ ID NO: 2.

13. The method of claim 12, further comprising operably linking said surface of said substrate to at least one additional adhesion ligand selected from the group consisting of SEQ ID NOs: 8, 11 and 18 and combinations thereof.

14. The method of claim 12, wherein said substrate comprises a material suitable for use in a medical device or implant.

15. The method of claim 12, wherein the endothelial cell capture and support surface comprises or is incorporated into an in vitro testing device.

16. The method of claim 15, wherein said in vitro testing device is a microfluidic chip.

17. The method of claim 12, wherein said substrate is selected from the group consisting of biomimetic material, a polymer, hydrogel, material suitable for use in a medical device or implant and decellularized extracellular matrix (dECM).

18. An endothelial cell capture and support surface produced by the method of claim 12.

19. A medical device or implant comprising the composition of claim 1.

20. The medical device or implant of claim 19, wherein said medical device or implant is a vascular graft, stent, shunt, or valve.

* * * * *